United States Patent [19]

Clark et al.

[11] Patent Number: 5,212,195

[45] Date of Patent: May 18, 1993

[54] SUBSTITUTED INDOLE ANTAGONISTS DERIVATIVES WHICH ARE ANGIOTENSIN II

[75] Inventors: Robin D. Clark, Palo Alto; David E. Clarke; Lawrence E. Fisher, both of Mountain View; Alam Jahangir, San Jose, all of Calif.

[73] Assignee: Syntex (U.S.A.) Inc., Palo Alto, Calif.

[21] Appl. No.: 882,390

[22] Filed: May 13, 1992

[51] Int. Cl.$^5$ ............... A61K 31/41; C07D 257/04
[52] U.S. Cl. ................... 514/381; 548/252; 548/253; 548/254
[58] Field of Search ............. 548/252, 253, 254; 514/381

[56] References Cited

U.S. PATENT DOCUMENTS

| | | | |
|---|---|---|---|
| 4,333,943 | 6/1982 | Kurchacova et al. | 548/253 |
| 4,880,804 | 11/1989 | Carini et al. | 514/234.5 |
| 5,015,651 | 5/1991 | Carini et al. | 514/381 |
| 5,053,329 | 10/1991 | Chen et al. | 435/119 |
| 5,124,335 | 6/1992 | Patchett et al. | 514/300 |

FOREIGN PATENT DOCUMENTS 0400835 12/1990 European Pat. Off.

OTHER PUBLICATIONS

Identification of Angiotensin II Receptor Subtypes, by Chiu et al., *Biochemical and Biophysical Research Communications*, vol. 165, 196-203 (1989).

Primary Examiner—Bernard Dentz
Attorney, Agent, or Firm—Brian Lewis; David A. Lowin; Tom M. Moran

[57] ABSTRACT

Compound of the Formula (I), (II), or (III):

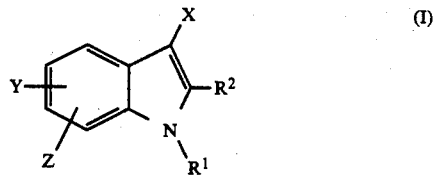

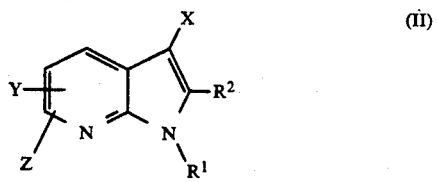

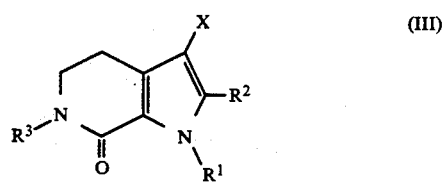

wherein:
$R^1$ is lower alkyl or 2''-(1H-tetrazol-5-yl)biphenyl-4'-ylmethyl;
$R^2$ is lower alkyl when $R^1$ is 2''-(1H-tetrazol-5-yl)biphenyl-4'-ylmethyl; or $R^2$ is 2''-(1H-tetrazol-5-yl)biphenyl-4'-ylmethyl when $R^1$ is lower alkyl;
$R^3$ is hydrogen or lower alkyl;
X is hydrogen, lower alkyl, halogen, —C(O)CF$_3$, —CO$_2$R$^4$, or —C(O)NR$^5$R$^6$;
Y is hydrogen, lower alkyl, lower alkoxy, hydroxy, halogen, or —CO$_2$R$^4$;
Z is hydrogen, lower alkyl, lower alkoxy, or halogen; with the proviso that Y and Z cannot be attached to the nitrogen atom in Formula (II); wherein
$R^4$ is hydrogen or lower alkyl;
$R^5$ is hydrogen or lower alkyl;
$R^6$ is hydrogen or lower alkyl; or
$R^5$ and $R^6$ taken together with the nitrogen to which they are attached represent a heterocycle;

and pharmaceutically acceptable salts thereof, exhibit useful pharmacological properties, and are particularly useful as angiotensin II antagonists.

11 Claims, No Drawings

SUBSTITUTED INDOLE ANTAGONISTS DERIVATIVES WHICH ARE ANGIOTENSIN II

BACKGROUND OF THE INVENTION

1. Field of the Invention

The present invention relates to substituted indole, azaindole and tetrahydro-1H-pyrrolo[2,3-c]pyridin-7-one compounds and derivatives thereof, useful as angiotensin II antagonists, particularly effective in the control of smooth and cardiac muscle contraction, especially for the treatment of cardiovascular disorders such as hypertension and congestive heart failure. Additionally, the compounds of the present invention are useful for the treatment of chronic renal failure, cognitive and affective disorders, and disorders of the alimentary tract.

2. Related Disclosures

The renin-angiotensin system is a fundamental physiological mechanism for regulating blood pressure in mammals. Angiotensinogen is secreted into the bloodstream by the liver. Angiotensinogen is then cleaved by the protease renin to yield the decapeptide angiotensin I, which in turn is hydrolyzed by angiotensin converting enzyme (ACE) to the octapeptide angiotensin II. Angiotensin I is inactive in the cardiovascular system, but angiotensin II has numerous cardiovascular-renal activities. For example, it stimulates the adrenal cortex to secrete aldosterone, which causes the kidneys to retain sodium and water, increasing blood pressure. It causes vasoconstriction. It also facilitates neurotransmission in the sympathetic nervous system.

The effects of angiotensin II, such as arteriolar vasoconstriction, contraction of gastro-intestinal smooth muscle, aldosterone secretion, glycogenolysis, alteration of renal function and CNS effects, are mediated by the activation of specific angiotensin II receptors on smooth and cardiac muscle, adrenal medulla, brain, liver and kidney. Angiotensin II receptors are categorized into subtypes, for example the AT-1 and AT-2 subtypes. It is evident that disease states associated with activation of angiotensin II receptors could be usefully treated by compounds possessing angiotensin II antagonist activity.

Various angiotensin II receptor antagonists are known. See, for example, U.S. Pat. Nos. 4,333,943, 4,880,804, 5,053,329, and European Patents 0 245 637, 0 253 310, and 0 291 969, and also Wong et al., Hypertension 15:459 (1990), *J. Pharmacol. Exp. Ther.* 256:211 (1990), and Chiu et al., *Biochem. Biophys. Res. Comm.* 165:196–203 (1989).

SUMMARY OF THE INVENTION

A first aspect of the present invention relates to compounds of the Formula (I), (II) and (III):

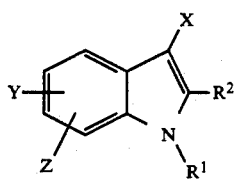 (I)

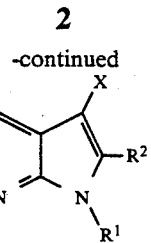 (II)

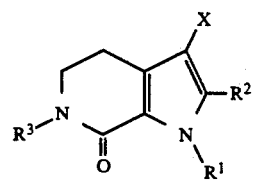 (III)

wherein:

$R^1$ is lower alkyl or 2''-(1H-tetrazol-5-yl)biphenyl-4'-ylmethyl;

$R^2$ is lower alkyl when $R^1$ is 2''-(1H-tetrazol-5-yl)biphenyl-4'-ylmethyl; or $R^2$ is 2''-(1H-tetrazol-5-yl)biphenyl-4'-ylmethyl when $R^1$ is lower alkyl;

$R^3$ is hydrogen or lower alkyl;

X is hydrogen, lower alkyl, halogen, $-C(O)CF_3$, $-CO_2R^4$, or $-C(O)NR^5R^6$;

Y is hydrogen, lower alkyl, lower alkoxy, hydroxy, halogen, or $-CO_2R^4$;

Z is hydrogen, lower alkyl, lower alkoxy, or halogen; with the proviso that Y and Z cannot be attached to the nitrogen atom in Formula (II);

wherein $R^4$ is hydrogen or lower alkyl;

$R^5$ is hydrogen or lower alkyl;

$R^6$ is hydrogen or lower alkyl; or $R^5$ and $R^6$ taken together with the nitrogen to which they are attached represent a heterocycle;

and the pharmaceutically acceptable salts thereof.

A second aspect of this invention relates to pharmaceutical compositions containing at least one compound of Formula (I), (II) or (III), and one or more pharmaceutically acceptable excipients.

A third aspect of this invention relates to methods for treating angiotensin II receptor-related disorders in a mammal by administering an effective amount of a compound of Formula (I), (II) or (III), or a composition containing a compound of Formula (I), (II) or (III), to the mammal. In one embodiment, the angiotensin II receptor-related disorder treated is a cardiovascular disease, more particularly hypertension or congestive heart failure. In another embodiment, the angiotensin II receptor-related disorder treated is chronic renal failure or disorders of the alimentary tract. In yet another embodiment, the invention relates to methods for treating cognitive and affective disorders.

A fourth aspect of the invention relates to methods for the preparation of the compounds of Formula (I), (II) and (III).

A fifth aspect of the invention relates to intermediates of the Formula (1), (2) and (3), shown below:

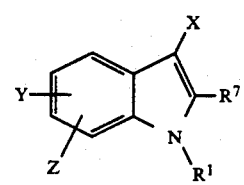 (1)

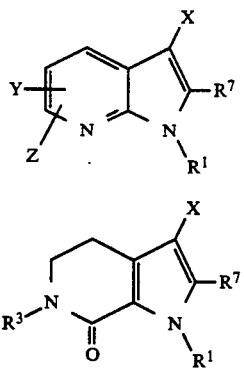

wherein $R^1$ and $R^7$ are different and are either lower alkyl or 2''-cyanobiphenyl-4'-ylmethyl, and X, Y, Z, $R^1$ and $R^3$ are as defined above.

DETAILED DESCRIPTION OF THE INVENTION

Definitions

As used herein:

"Alkyl" means a branched or unbranched saturated hydrocarbon chain containing 1 to 12 carbon atoms, such as methyl, ethyl, propyl, tert-butyl, n-hexyl, n-octyl, n-decyl, and the like.

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Lower alkoxy" means the group —O—R wherein R is lower alkyl is as defined above.

The definition "$R^5$ and $R^6$ taken together with the nitrogen to which they are attached is a heterocycle" as used herein is intended to include saturated monovalent monocyclic radicals containing 3–7 carbon atoms and one nitrogen atom, such as azetidine, azolidine, piperidine, 4-methylpiperidine, hexamethyleneimine, heptamethyleneimine, and the like.

The term "halo" means fluoro, bromo, chloro or iodo, unless otherwise indicated.

The terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

The compounds of Formula (I), (II) and (II) form base addition salts by virtue of the presence of a 1H-tetrazol-5-yl group, and/or the presence of —CO$_2$H group. The term "pharmaceutically acceptable salt" means any salt derived from an inorganic or organic base chosen not to be biologically or otherwise undesirable. The term "pharmaceutically acceptable cation" means the cation of such base addition salts. The cations derived from inorganic bases include sodium, potassium, lithium, ammonium, calcium, magnesium and the like. Cations derived from organic bases include those formed from primary, secondary and tertiary amines, such as isopropylamine, diethylamine, trimethylamine, pyridine, cyclohexylamine, ethylene diamine, monoethanolamine, diethanolamine, triethanolamine and the like.

"Optional" or "optionally" means that the subsequently described event or circumstance may or may not occur, and that the description includes instances where said event or circumstance occurs and instances in which it does not. For example, "optionally followed by converting the free acid to the base addition salt" means that said conversion may or may not be carried out in order for the process described to fall within the invention, and the invention includes those processes wherein the free base is converted to the acid addition salt and those processes in which it is not.

The term "mammal" includes humans and all domestic and wild mammals, including, without limitation, cattle, horses, swine, sheep, goats, dogs, cats, rabbits, and the like.

The term "treatment" as used herein covers any treatment of a disease in a mammal, particularly a human, and includes:

(i) preventinq the disease from occurring in a subject which may be predisposed to the disease but has not yet been diagnosed as having it;

(ii) inhibiting the disease, i.e. arresting its development; or (iii) relieving the disease, i.e. causing regression of the disease.

The term "a disease-state that is alleviable by treatment with an angiotensin II antagonist" as used herein is intended to cover all disease states which are generally acknowledged in the art to be usefully treated with angiotensin II antagonists in general, and those disease states which have specifically been found to be usefully treated by the specific compounds of our invention, the compounds of Formula (I), (II) and (III). Such disease states include, but are not limited to, cardiovascular disorders such as hypertension and congestive heart failure, chronic renal failure, cognitive and affective disorders, and disorders of the alimentary tract, for example inflammatory bowel disease.

The term "q.s." means adding a quantity sufficient to achieve a stated function, e.g., to bring a solution to the desired volume (i.e., 100%).

The term "effective amount" means a dosage sufficient to provide treatment for the disease state being treated. This will vary depending on the patient, the disease and the treatment being effected.

The naming and numbering of the compounds of the present invention are illustrated below.

As defined in the Summary of the Invention, either $R^1$ or $R^2$ is a group named as 2''-(1H-tetrazol-5-yl)biphenyl-4'-ylmethyl. The structure and the numbering of this group is illustrated below:

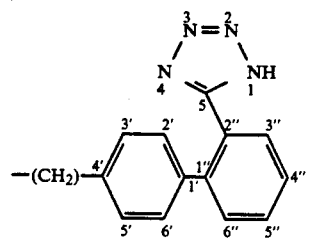

The tetrazole group is illustrated with the hydrogen atom at the 1-position. However, the tetrazole group is tautomeric, and consequently the hydrogen may be present at any of the 1-, 2-, 3- and 4-positions.

A compound of Formula (I) is numbered as follows:

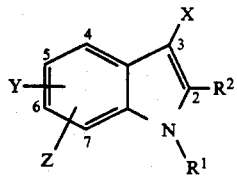

The compound of Formula (I) where X is —CO$_2$H, Y and Z are hydrogen, R$^1$ is n-butyl, and R$^2$ is 2''-(1H-tetrazol-5-yl)biphenyl-4'-ylmethyl, is named:

1-(n-butyl)-2-[2''-(1H-tetrazol-5-yl)biphenyl-4'-ylmethyl]indole-3-carboxylic acid.

The compound of Formula (I) where X and Z are hydrogen, Y is 7—CP$_2$H, R$^1$ is 2''-(1H-tetrazol-5-yl)biphenyl-4'-ylmethyl, and R$^2$ is ethyl is named:

2-ethyl-1-[2''-(1H-tetrazol-5-yl)biphenyl-4'-ylmethyl]indole-7-carboxylic acid.

A compound of Formula (II) is numbered as follows:

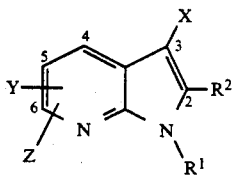

The compound of Formula (II) where X, Y and Z are hydrogen, R$^1$ is 2''-(1H-tetrazol-5-yl)biphenyl-4'-ylmethyl, and R$^2$ is n-butyl is named:

2-(n-butyl)-1-[2''-(1H-tetrazol-5-yl)biphenyl-4'-ylmethyl]-1H-pyrrolo[2,3-b]pyridine.

A compound of Formula (III) is numbered as follows:

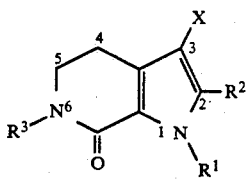

The compound of Formula (III) where X is hydrogen, R$^1$ is 2''-(1H-tetrazol-5-yl)biphenyl-4'-ylmethyl, R$^2$ is n-butyl, and R$^3$ is methyl, is named:

2-(n-butyl)-6-methyl-1-[2''-(1H-tetrazol-5-yl)biphenyl-4'-ylmethyl]-4,5,6,7-tetrahydro-1H-pyrrolo[2,3-c]pyridin-7-one.

Preferred Embodiments

Among the family of compounds of the present invention, one preferred category includes the compounds of Formula (I) where R$^1$ is lower alkyl and R$^2$ is 2''-(1H-tetrazol-5-yl)biphenyl-4'-ylmethyl, especially where Z is hydrogen. Within this category a preferred group includes the compounds where Y is hydrogen or lower alkoxy, especially where X is hydrogen or —CO$_2$R$^4$, and more especially where R$^1$ is n-butyl and R$^4$ is hydrogen.

Another preferred category includes the compounds of Formula (I) where R$^1$ is 2''-(1H-tetrazol-5-yl)biphenyl-4'-ylmethyl and R$^2$ is lower alkyl, especially where Z is hydrogen. Within this category a preferred group includes the compounds where X and Y are independently chosen from hydrogen and —CO$_2$R$^4$, especially where R$^2$ is n-butyl and R$^4$ is hydrogen A third preferred category includes the compounds of Formula (II) where R$^1$ is 2''-(1H-tetrazol-5-yl)biphenyl-4'-ylmethyl and R$^2$ is lower alkyl, especially where Z is hydrogen. Within this category a preferred group includes the compounds where X and Y are independently chosen from hydrogen and —CO$_2$R$^4$, especially where R$^2$ is n-butyl and R$^4$ is hydrogen.

A fourth preferred category includes the compounds of Formula (II) where R$^1$ is lower alkyl and R$^2$ is 2''-(1H-tetrazol-5-yl)biphenyl-4'-ylmethyl, especially where Z is hydrogen. Within this category a preferred group includes the compounds where X and Y are independently chosen from hydrogen and —CO$_2$R$^4$, especially where R$^1$ is n-butyl and R$^4$ is hydrogen.

A fifth preferred category includes the compounds of Formula (III) where R$^1$ is 2''-(1H-tetrazol-5-yl)biphenyl-4'-ylmethyl and R$^2$ is lower alkyl. Within this category a preferred group includes the compounds where X is hydrogen or —CO$_2$R$^4$ and R$^2$ is n-butyl.

A sixth preferred category includes the compounds of Formula (III) where R$^1$ is lower alkyl and R$^2$ is 2''-(1H-tetrazol-5-yl)biphenyl-4'-ylmethyl. Within this category a preferred group includes the compounds where X is hydrogen or —CO$_2$R$^4$ and R$^1$ is n-butyl.

At present, the most preferred compounds are:

1-(n-butyl)-2-[2''-(1H-tetrazol-5-yl)biphenyl-4'-ylmethyl]-indole-3-carboxylic acid;

2-(n-butyl)-1-[2''-(1H-tetrazol-5-yl)biphenyl-4'-ylmethyl]indole-7-carboxylic acid;

2-(n-butyl)-1-[2''-(1H-tetrazol-5-yl)biphenyl-4'-ylmethyl]-1H-pyrrolo[2,3-b]pyridine; and 2-(n-butyl)-1-[2''-(1H-tetrazol-5-yl)biphenyl-4'-ylmethyl]-4,5,6,7-tetrahydro-1H-pyrrolo[2,3-c]pyridin-7-one.

PREPARATION OF COMPOUNDS OF FORMULA (I), (II) and (III)

The compounds of Formula (I) where R$^1$ is lower alkyl and R$^2$ is 2''-(1H-tetrazol-5-yl)biphenyl-4'-ylmethyl, identified as Formula (Ia), are prepared from the intermediates of Formula (K) or (L), the preparation of which is shown below in Reaction Scheme I.

The compounds of Formula (I) where R$^1$ is 2''-(1H-tetrazol-5-yl)biphenyl-4'-ylmethyl and R$^2$ is lower alkyl, identified as Formula (Ib), are prepared from the intermediates of Formula (R) or (V), the preparation of which is shown below in Reaction Schemes II and III. Reaction Scheme III is the preferred procedure for preparing compounds of Formula (Ib) in which Y is at the 7-position. This is because a substituent at the 7 position may sterically hinder the desired coupling of the cyanobiphenylmethyl moiety to the 1 position of the indole. In Reaction Scheme III, this problem is avoided because the cyanobiphenylmethyl moiety is attached to the nitrogen before the formation of the fused heterocycle.

The compounds of Formula (II) where R$^1$ is 2''-(1H-tetrazol-5-yl)biphenyl-4'-ylmethyl and R$^2$ is lower alkyl, are prepared from the intermediates of Formula (AC), the preparation of which is shown below in Reaction Scheme IV.

The compounds of Formula (III) where $R^1$ is 2"-(1H-tetrazol-5-yl)biphenyl-4'-ylmethyl and $R^2$ is lower alkyl, are prepared from the intermediates of Formula (AI) or (AJ), the preparation of which is shown below in Reaction Scheme V.

1. PREPARATION OF (K) AND (L) WHERE $R^1$ IS LOWER ALKYL

The compounds of Formula (Ia) may be prepared from the intermediates of Formulae (K) and (L), where $R^1$ is lower alkyl, the preparation of which is shown below in Reaction Scheme I.

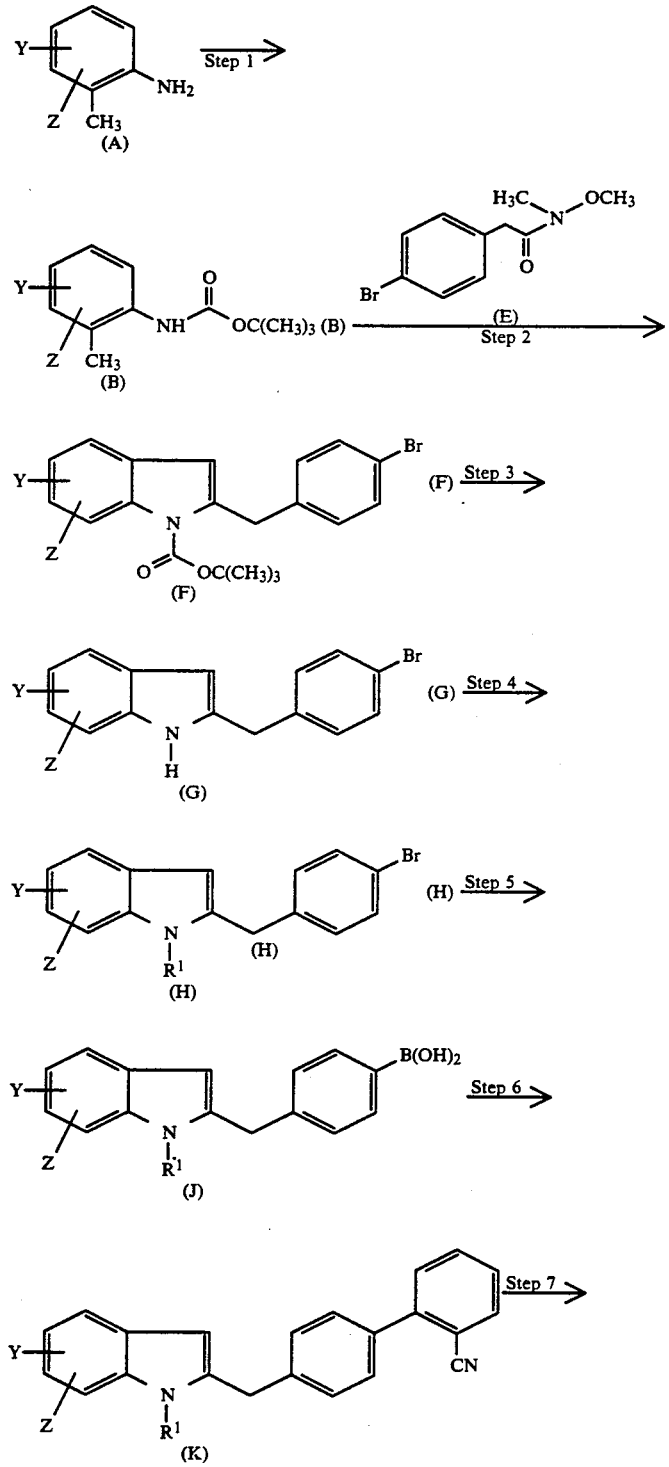

Reaction Scheme I

-continued
Reaction Scheme I

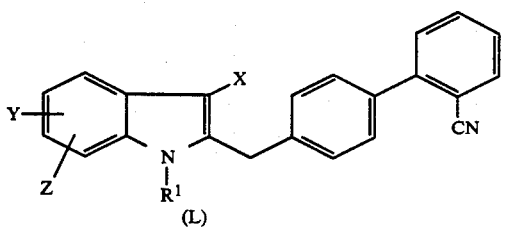

where R¹ is lower alkyl, and X, Y and Z are as defined in the Summary of the Invention.

Starting Materials.

The substituted aniline starting materials of Formula (A) are commercially available, for example for Aldrich Chemical Company. Alternatively, the substituted aniline compounds of Formula (A) can be prepared from commercially available substituted anilines by conventional means.

The reactant of Formula (E), N-methyl-N-methoxy-p-bromophenylacetylamide, used in step 2 of Reaction Scheme I, may be prepared according to the general method described in Nahm, S. and Weinreb, S. *Tet. Lett.* 22:3815-3818 (1981). Most preferably, this amide is prepared as follows:

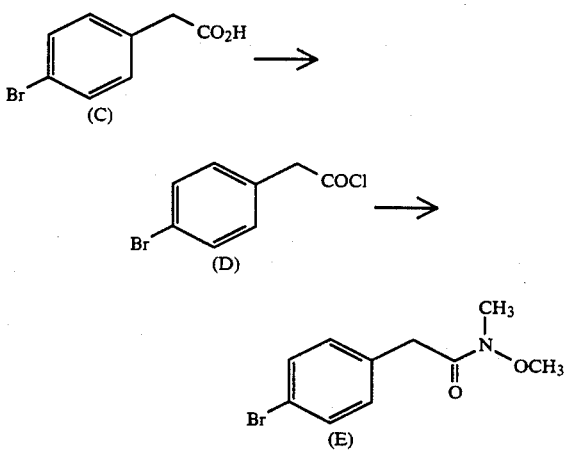

Step I of the preparation of N-methyl-N-methoxy-p-bromophenylacetylamide (E) uses p-bromophenylacetic acid, the starting material of Formula (C), which is commercially available, for example, from Aldrich Chemical Company.

Initially, oxalyl chloride is added to an equimolar amount of p-bromophenylacetic acid (C) in an inert solvent, preferably methylene chloride, at about room temperature, with a catalytic amount of dimethylformamide. The mixture is stirred for about 30 minutes, after which the product, p-bromophenylacetyl chloride (D), is isolated by conventional means.

Then p-bromophenylacetyl chloride (D) is dissolved in an inert solvent, preferably methylene chloride, cooled, and reacted with N-methyl-O-methylhydroxylamine hydrochloride in the same inert solvent, preferably methylene chloride, in the presence of a tertiary amine, preferably triethylamine. The product, N-methyl-N-methoxy-p-bromophenylacetylamide (E), is isolated by conventional means.

The 2-cyanobromobenzene used in step 6 of Reaction Scheme I is commercially available from Aldrich.

The trialkyl tin azide used in step 8 is prepared as described in Kricheldorf and Leppert, *Synthesis*, pp 329-330 (1976).

Preparation of Compounds of Formula (B)

To prepare a compound of Formula (B), a compound of Formula (A) is reacted with about 1-2 molar equivalents, preferably about 1 molar equivalent, of di-t-butyl-dicarbonate in an inert solvent (such as ether, dichloromethane, or tetrahydrofuran, preferably tetrahydrofuran). The reaction is carried out at a temperature of about 60° C. to 100° C., preferably at about 80° C., for about 2 to 6 hours, preferably 4 hours. When the reaction is substantially complete the t-butyl-carbamate of Formula (B) is isolated by conventional means.

Preparation of Compounds of Formula (F)

To prepare a compound of Formula (F), a compound of Formula (B) is first reacted with about 2 molar equivalents of a strong base (such as a butyllithium, preferably sec-butyllithium), in an ethereal solvent (such as diglyme, ether, or tetrahydrofuran, preferably tetrahydrofuran), at a temperature of about −30° C. to −50° C., preferably at about −40° C. After addition of the base, the temperature is lowered to about −70° C. to −100° C., preferably at about −75° C.

To the lithium dianion thus formed is added about 1 to 1.5 molar equivalents, preferably about 1 molar equivalent, of the compound of Formula (E) (N-methyl-N-methoxy-p-bromophenylacetylamide) in an ethereal solvent, preferably tetrahydrofuran, maintaining the temperature at about −80° C. to −50° C., preferably at about −60° C., for about 5 minutes to 1 hour, preferably about 10 minutes. When the reaction is substantially complete an uncyclized intermediate is isolated by conventional means, and dissolved in an inert aprotic solvent (such as ether, tetrahydrofuran, or methylene chloride; preferably methylene chloride), and about 0.1 to 2 molar equivalents, preferably about 1 molar equivalent, of trifluoroacetic acid is added. The reaction is carried out at about room temperature, for about 5 minutes to 1 hour, preferably about 30 minutes. When the reaction is substantially complete the t-butyl-carboxyindole of Formula (F) is isolated by conventional means.

Preparation of Compounds of Formula (G)

To prepare a compound of Formula (G), a compound of Formula (F) is reacted with an excess of a base (such as potassium hydroxide, ammonium hydroxide, or sodium hydroxide; preferably sodium hydroxide) in water and an organic solvent (such as methanol, propanol, or ethanol; preferably ethanol), at a temperature of about

Preparation of Compounds of Formula (H) where $R^1$ is lower alkyl

To prepare a compound of Formula (H) where $R^1$ is lower alkyl, a compound of Formula (G) is first reacted with 1 to 1.5 molar equivalents, preferably about 1.1 molar equivalents, of an alkali metal hydride (such as lithium hydride, potassium hydride, or sodium hydride; preferably sodium hydride) in a polar solvent (such as acetamide, DMSO (dimethyl sulfoxide), or DMF (dimethylformamide); preferably DMF). The reaction is carried out at a temperature of $-10°$ C. to $20°$ C., preferably about $0°$ C., for about 5 minutes to 1 hour, preferably about 10 minutes. The anion thus formed is then reacted with about 1 to 1.5 molar equivalents, preferably about 1 molar equivalent, of a lower alkyl halide, preferably a lower alkyl iodide, for about 15 to 60 minutes, preferably about 30 minutes. When the reaction is substantially complete the 1-lower alkyl-2-(p-bromophenylmethyl)indole of Formula (H) where $R^1$ is lower alkyl is isolated by conventional means.

Preparation of Compounds of Formula (J) where $R^1$ is lower alkyl

To prepare a compound of Formula (J) where $R^1$ is lower alkyl, a compound of Formula (H) where $R^1$ is lower alkyl is first reacted with 1 to 1.5 molar equivalents, preferably about 1.1 molar equivalents, of an alkyl lithium base, preferably n-butyllithium, in an ethereal solvent (such as ether, monoglyme, or tetrahydrofuran; preferably tetrahydrofuran). The reaction is carried out at a temperature of $-100°$ C. to $-50°$ C., preferably about $-70°$ C., for about 5 minutes to 1 hour, preferably about 15 minutes. The anion thus formed is then reacted with about 1 to 2 molar equivalents, preferably about 1.5 molar equivalents, of an alkyl borate (such as triethyl borate, trimethyl borate, or tributyl borate, preferably tributyl borate), allowing the reaction mixture to warm to about $0°$ C. When the reaction is substantially complete the 2-[4'-(dihydroxyboron)phenylmethyl]indole of Formula (J) where $R^1$ is lower alkyl is isolated by conventional means.

Preparation of Compounds of Formula (K) where $R^1$ is lower alkyl

To prepare a compound of Formula (K) where $R^1$ is lower alkyl, a compound of Formula (J) where $R^1$ is lower alkyl is reacted with 1 to 1.5 molar equivalents, preferably about 1.1 molar equivalents, of a 1-cyano-2-halobenzene (preferably 1-cyano-2-bromobenzene) and a transition metal catalyst (such as di-[triphenyl phosphine]palladium chloride, palladium on carbon, or tetrakis[triphenylphosphine]palladium, preferably tetrakis[triphenylphosphine]palladium). The reaction is carried out in an inert solvent (such as tetrahydrofuran, ethanol, and/or toluene; preferably a mixture of toluene and ethanol), in the presence of an excess of a mild base (such as sodium or potassium carbonate, or sodium bicarbonate, preferably sodium carbonate). The reaction is carried out at a temperature of $60°$ C. to reflux, preferably at about reflux for 6 to 48 hours, preferably about 24 hours. When the reaction is substantially complete the 2-(4''-cyanobiphenyl-4'-ylmethyl)-indole of Formula (K) where R is lower alkyl is isolated by conventional means.

Preparation of Compounds of Formula (L) where $R^1$ is lower alkyl and X is $-CO_2H$ To prepare a compound of Formula (L) where $R^1$ is lower alkyl and X is $-CO_2H$, a compound of Formula (K) where $R^1$ is lower alkyl is reacted with 1 to 3 molar equivalents, preferably about 1.5 molar equivalents, of phosgene. The reaction is carried out in an inert solvent (such as ether, methylene chloride, or tetrahydrofuran; preferably tetrahydrofuran) at $-20°$ C. to $10°$ C., preferably about $0°$ C., for about 8 to 48 hours, preferably overnight. When the reaction is substantially complete the 3-carboxyindole of Formula (L) where $R^1$ is lower alkyl and X is $-CO_2H$ is isolated by conventional means.

Preparation of Compounds of Formula (L) where $R^1$ is lower alkyl and X is $-CO_2R^4$ To prepare a compound of Formula (L) where $R^1$ is lower alkyl and X is $-CO_2R^4$, in which $R^4$ is lower alkyl, the solution of a compound of Formula (L) where X is $-COCl$ in dichloromethane, prepared as shown above, is cooled to $0°$ to $10°$ C., preferably about $5°$ C., and reacted with an alcohol of formula $R^4OH$, where $R^4$ is lower alkyl. When the reaction is substantially complete, the 3-(carbo-loweralkoxy)indole derivative of Formula (Q), where $R^1$ is lower alkyl and X is $-CO_2R^4$, in which $R^4$ is lower alkyl, is isolated and purified by conventional means, preferably chromatography.

Preparation of Compounds of Formula (L) where $R^1$ is lower alkyl and X is $-CONR^5R^6$ To prepare a compound of Formula (L) where $R^1$ is lower alkyl and X is $-CONR^5R^6$, in which $R^5$ and $R^6$ are as defined in the Summary of the Invention, the procedure shown above is followed, substituting an amine of formula $R^5R^6NH$ for the alcohol of formula $R^4OH$.

Preparation of Compounds of Formula (L) where $R^1$ is lower alkyl and X is $-COCF_3$ To prepare a compound of Formula (L) where $R^1$ is lower alkyl and X is $-COCF_3$, a compound of Formula (K) where $R^1$ is lower alkyl is reacted with 1 to 1.5 molar equivalents, preferably about 1.1 molar equivalents, of trifluoroacetic anhydride. The reaction is carried out in an aprotic solvent (such as ether, tetrahydrofuran, or DMF; preferably DMF) at $-10°$ C. to $20°$ C., preferably about $0°$ C., for about 5 to 30 minutes, preferably about 10 minutes. When the reaction is substantially complete the 3-trifluoroacetylindole of Formula (L) where $R^1$ is lower alkyl and X is $-COCF_3$ is isolated by conventional means.

Preparation of Compounds of Formula (L) where $R^1$ is lower alkyl and X is Halo To prepare a compound of Formula (L) where $R^1$ is lower alkyl and X is halo, a compound of Formula (K) where $R^1$ is lower alkyl is reacted with 1 to 1.5 molar equivalents, preferably about 1.1 molar equivalents, of an N-halosuccinimide. The reaction is carried out in an aprotic solvent (such as ether, tetrahydrofuran, or DMF; preferably DMF) at $0°$ C. to $30°$ C., preferably about $20°$ C., for about 5 to 30 hours, preferably about 16 hours. When the reaction is substantially complete the 3-halo compound of Formula (L) where $R^1$ is lower alkyl and X is halo is isolated by conventional means.

2. PREPARATION OF (P) AND (Q) WHERE $R^2$ IS LOWER ALKYL

The compounds of Formula (Ib) may be prepared from the intermediates of Formula (R), where $R^2$ is lower alkyl, the preparation of which is shown below in Reaction Scheme II.

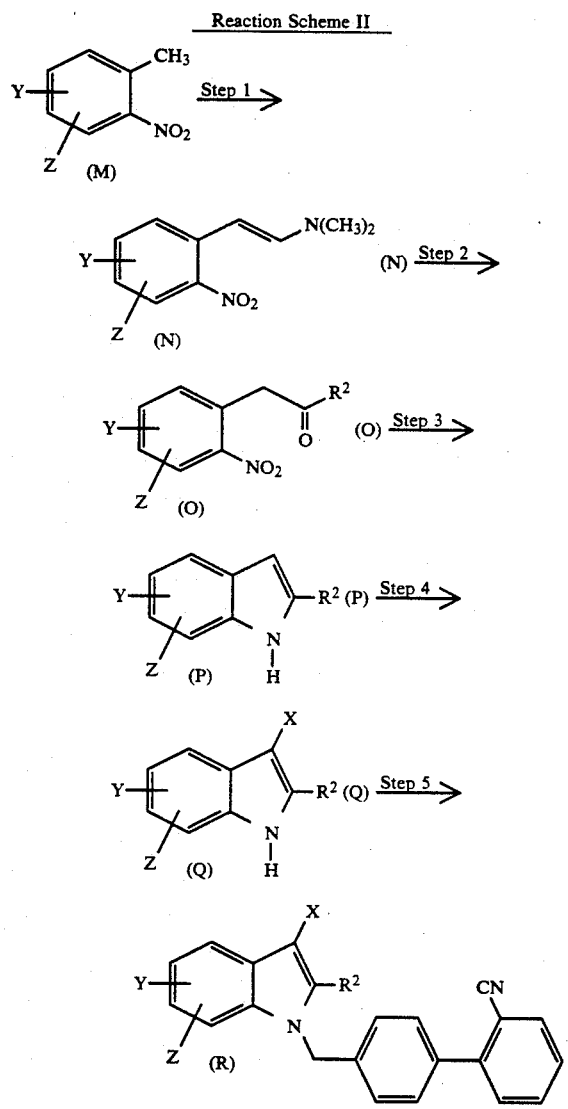

Reaction Scheme II

Starting Materials o-Nitrotoluene derivatives of Formula (M) where Y and Z are chosen from, for example, hydrogen, halo, lower alkoxy, and hydroxy, are commercially available, for example from Aldrich Chemical Company. Alternatively, as is well known in the art, the o-nitrotoluene derivatives of Formula (M) where Y is —$CO_2H$ can be prepared from commercially available o-nitrotoluenes appropriately substituted by carboxyl. Such acids may be converted by methods well known in the art to produce compounds where Y is an ester or an amide.

The 4-halomethyl-2'-cyanobiphenyl compounds used in step 5 (and elsewhere), may be prepared by a number of known methods, most preferably as follows: Equimolar amounts of 2-bromobenzylnitrile and 4-methylbenzylboronic acid are combined with tetrakis[triphenylphosphine]palladium, toluene, sodium carbonate and ethanol and refluxed vigorously, with stirring for 6 to 12 hours, preferably overnight. The mixture is allowed to cool to 10° to 30° C., preferably ambient temperature and hydrogen peroxide is added. The mixture is stirred, extracted with ether, washed with water, and dried over magnesium sulphate to produce an oil, 4-methyl-2'-cyanobiphenyl. To this oil, equimolar amounts of N-bromosuccinimide and azaisobutylnitrile are added, in a nonpolar solvent (such as ether, cyclohexane, or carbon tetrachloride; preferably carbon tetrachloride), and the mixture is heated under reflux for 1 to 4 hours, preferably 2 hours. The mixture is cooled and filtered, and the solvent is extracted to yield 4-bromomethyl-2'-cyano-biphenyl.

Certain substituted indoles of Formula (P), used in step 4 of Reaction Scheme II, are also available commercially, e.g, 2-methylindole, indole-2-carboxylic acid, and indole-3-propanoic acid, from Kawaken Fine Chemicals Co., Ltd., Tokyo, Japan.

Preparation of Compounds of Formula (N)

To prepare a compound of Formula (N), a compound of Formula (M) is reacted with an equivalent amount of N,N-dimethylformamide dimethylacetal in an aprotic solvent (such as ether, tetrahydrofuran, or DMF; preferably DMF). The reaction is carried out at a temperature of 100° C. to about reflux, preferably about reflux temperature, for about 24 to 100 hours, preferably about 72 hours. When the reaction is substantially complete the nitrostyrene derivative of Formula (N) is isolated by conventional means.

Preparation of Compounds of Formula (O) where $R^2$ is lower alkyl

To prepare a compound of Formula (O) where $R^2$ is lower alkyl, a compound of Formula (N) is reacted with 1 to 1.5 molar equivalents, preferably about 1.1 molar equivalents, of an acyl halide of formula $R^1COCl$, where $R^1$ is lower alkyl, in the presence of excess of a tertiary base (such as triethylamine or pyridine, preferably pyridine). The reaction is carried out in a chlorinated organic solvent (such as chloroform, 1,2-dichloroethane, or dichloromethane, preferably dichloromethane), at a temperature of 20° C. to reflux, preferably at about reflux temperature, for about 5 to 72 hours, preferably about 24 hours. The product of this reaction is isolated by conventional means, and is dissolved in a mixture of an inert solvent (such as DMF, tetrahydrofuran, or dioxane, preferably dioxane) and water, and the resulting mixture is heated at 50° C. to reflux, preferably at about reflux, for 8 to 24 hours, preferably 16 hours. When the reaction is substantially complete the nitrophenyl derivative of Formula (O) where $R^2$ is lower alkyl is isolated and purified by conventional means, preferably chromatography.

Preparation of Compounds of Formula (P) where $R^2$ is lower alkyl

To prepare a compound of Formula (P) where $R^2$ is lower alkyl, a compound of Formula (O) where $R^2$ is lower alkyl is reacted with 2 to 20 molar equivalents, preferably about 11 molar equivalents, of a reducing metal (such as nickel, iron, or zinc dust, preferably zinc dust) in an acid solvent (such as propanoic acid, butanoic acid, or acetic acid, preferably acetic acid). The reaction is carried out at a temperature of about 60° to 100° C., preferably at about 90° C., for about 8 to 32 hours, preferably about 16 hours. When the reaction is substantially complete the indole derivative of Formula (P) where $R^2$ is lower alkyl is isolated and purified by conventional means, preferably chromatography.

Preparation of Compounds of Formula (Q) where $R^2$ is lower alkyl and X is —$CO_2H$ To prepare a compound of Formula (Q) where $R^2$ is lower alkyl and X is —$CO_2H$, a compound of Formula (P) where $R^2$ is lower alkyl is reacted with 1 to 3 molar equivalents, preferably about 1.5 molar equivalents, of phosgene. The reaction is carried out in an inert solvent (such as ether, methylene chloride, or tetrahydrofuran; preferably tetrahydrofuran) at −20° C. to 10° C., preferably about 0°–5° C., for about 8 to 48 hours, preferably overnight. When the reaction is substantially complete, water is added and the 3-carboxyindole derivative of Formula (Q) where $R^2$ is lower alkyl and X is —$CO_2H$ is isolated and purified by conventional means, preferably chromatography.

Preparation of Compounds of Formula (Q) where $R^2$ is lower alkyl and X is —$CO_2R^4$ To prepare a compound of Formula (Q) where $R^2$ is lower alkyl and X is —$CO_2R^4$, in which $R^4$ is lower alkyl, the solution of a compound of Formula (Q) where X is —COCl in dichloromethane, prepared as shown above, is cooled to 0° to 10° C., preferably about 5° C., and reacted with an alcohol of formula $R^4OH$, where $R^4$ is lower alkyl. When the reaction is substantially complete, the 3-(carbo-loweralkoxy)indole derivative of Formula (Q), where $R^2$ is lower alkyl and X is —$CO_2R^4$, in which $R^4$ is lower alkyl, is isolated and purified by conventional means, preferably chromatography.

Preparation of Compounds of Formula (Q) where $R^2$ is lower alkyl and X is —$CONR^5R^6$ To prepare a compound of Formula (Q) where $R^2$ is lower alkyl and X is —$CONR^5R^6$, in which $R^5$ and $R^6$ are as defined in the Summary of the Invention, the procedure shown above is followed, substituting an amine of formula $R^5R^6NH$ for the alcohol of formula $R^4OH$.

Preparation of Compounds of Formula (Q) where $R^2$ is lower alkyl and X is —$COCF_3$ To prepare a compound of Formula (Q) where $R^2$ is lower alkyl and X is —$COCF_3$, a compound of Formula (P) where $R^2$ is lower alkyl is reacted with 1 to 1.5 molar equivalents, preferably about 1.1 molar equivalents, of trifluoroacetic anhydride. The reaction is carried out in an aprotic solvent (such as ether, tetrahydrofuran, or DMF; preferably DMF) at −10° C. to 20° C., preferably about 0° C., for about 5 to 30 minutes, preferably about 10 minutes. When the reaction is substantially complete the 3-trifluoroacetylindole of Formula (Q) where $R^2$ is lower alkyl and X is —$COCF_3$ is isolated by conventional means.

Preparation of Compounds of Formula (Q) where $R^2$ is lower alkyl and X is Halo To prepare a compound of Formula (Q) where $R^2$ is lower alkyl and X is halo, a compound of Formula (P) where $R^2$ is lower alkyl is reacted with 1 to 1.5 molar equivalents, preferably about 1.1 molar equivalents, of an N-halosuccinimide. The reaction is carried out in an aprotic solvent (such as ether, tetrahydrofuran, or DMF; preferably DMF) at 0° C. to 30° C., preferably about 20° C., for about 5 to 30 hours, preferably about 16 hours. When the reaction is substantially complete the 3-halo compound of Formula (Q) where $R^2$ is lower alkyl and X is halo is isolated by conventional means.

Preparation of Compounds of Formula (R) where $R^2$ is Lower Alkyl and X is Hydrogen, Halo, —$COCF_3$, —$CO_2R^4$ or —$CONR^5R^6$ To prepare a compound of Formula (R) where $R^2$ is lower alkyl and X is hydrogen, halo, —$COCF_3$, —$CO_2R^4$ or —$CONR^5R^6$, a compound of Formula (P) where X is hydrogen or a compound of Formula (Q) where X is halo, —$COCF_3$, —$CO_2R^4$ or —$CONR^5R^6$, is reacted with about 1 molar equivalent of an alkali metal hydride, preferably sodium hydride, at −5° C. to 20° C., preferably about 0° C. The reaction is carried out in a polar solvent (such as tetrahydrofuran, DMSO, or DMF, preferably DMF), for about 10 minutes to 2 hours, preferably about 30 minutes. The anion thus formed is then reacted with about 1 to 1.5 molar equivalents, preferably about 1.1 molar equivalents, of a 4-halomethyl-2'-cyanobiphenyl compound or 4-tosylmethyl-2'-cyanobiphenyl, allowing the temperature to rise to about 20° C. When the reaction is substantially complete, the 2''-cyanobiphenyl-4'ylmethylindole derivative of Formula (R) where $R^2$ is lower alkyl and X is —$CO_2R^4$ is isolated and purified by conventional means, preferably chromatography.

3. PREPARATION OF (V) WHERE Y IS —$CO_2R^4$

The compounds of Formula (Ib) may also be prepared from the intermediates of Formula (V) where Y is —$CO_2R^4$, where $R^4$ is lower alkyl, the preparation of which is shown below in Reaction Scheme III. This is the preferred procedure for preparing (Ib) where Y is at the 7-position.

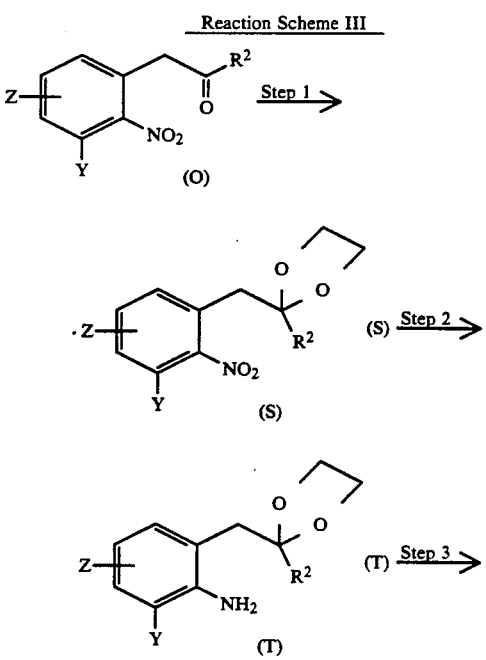

-continued
Reaction Scheme III

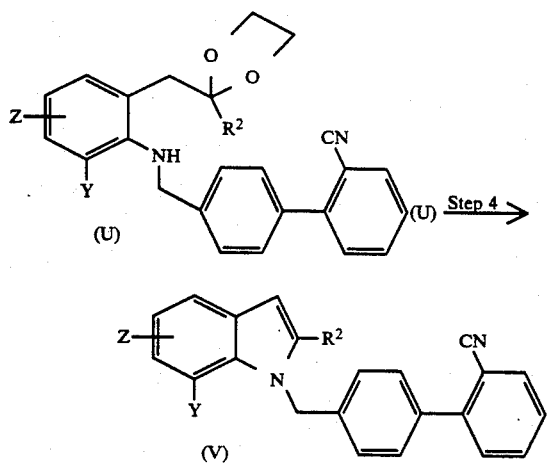

Preparation of Compounds of Formula (S) where $R^2$ is lower alkyl

To prepare a compound of Formula (S) where $R^2$ is lower alkyl, a compound of Formula (O) where $R^2$ is lower alkyl is reacted with about 1 to 5 molar equivalents, preferably about 1.5 molar equivalents, of ethylene glycol. The reaction is carried out in an aromatic solvent (such as benzene, xylene, or toluene; preferably toluene), in the presence of an acid catalyst, preferably p-toluenesulfonic acid, refluxing for 8 to 20 hours, preferably about 12 hours. When the reaction is substantially complete, the ethylene ketal derivative of Formula (S) where $R^2$ is lower alkyl, is isolated and purified by conventional means, preferably chromatography.

Preparation of Compounds of Formula (T) where $R^2$ is lower alkyl

To prepare a compound of Formula (T) where $R^2$ is lower alkyl, a compound of Formula (S) where $R^2$ is lower alkyl is hydrogenated in the presence of a transition metal catalyst. The reaction is carried out in a polar solvent (such as ethyl acetate, methanol, or ethanol, preferably ethanol), under hydrogen, in the presence of a transition metal catalyst (such as di[triphenylphosphine]palladium chloride, palladium on carbon, or tetrakis[triphenylphosphine]palladium, preferably palladium on carbon), at about room temperature for about 2 to 24 hours, preferably about 6 hours. When the reaction is substantially complete, the phenylamino derivative of Formula (T) where $R^2$ is lower alkyl, is isolated and purified by conventional means.

Preparation of Compounds of Formula (U) where $R^2$ is lower alkyl

To prepare a compound of Formula (U) where $R^2$ is lower alkyl, a compound of Formula (T) where $R^2$ is lower alkyl is reacted with about 1 to 1.5 molar equivalents, preferably about 1.1 molar equivalents, of a 4-halomethyl-2'-cyanobiphenyl compound (or a 4-tosylmethyl-2'-cyanobiphenyl compound) in the presence of about 1 to 1.5 molar equivalents, preferably about 1.1 molar equivalents, of a base (such as lithium carbonate, sodium carbonate, or potassium carbonate, preferably potassium carbonate). The reaction is carried out in a polar solvent (such as tetrahydrofuran, DMSO, or DMF, preferably DMF), at about 70°–100° C., preferably about 80°–90° C., for 6–48 hours, preferably about 16 hours. When the reaction is substantially complete, the cyanobiphenyl derivative of Formula (U) where $R^2$ is lower alkyl is isolated and purified by conventional means, preferably chromatography.

Preparation of Compounds of Formula (V)

To prepare a compound of Formula (V) where $R^2$ is lower alkyl, a compound of Formula (U) where $R^2$ is lower alkyl is dissolved in an organic solvent (such as dimethoxyethane, ether, or tetrahydrofuran, preferably tetrahydrofuran) containing an excess of a mineral acid (such as sulfuric acid, phosphoric acid, or hydrochloric acid, preferably hydrochloric acid) is stirred at 20°–80° C., preferably about 40° C., for 1–5 hours, preferably about 2 hours. When the reaction is substantially complete, the cyanobiphenyl derivative of Formula (V) where $R^2$ is lower alkyl, is isolated and purified by conventional means, preferably chromatography.

4. PREPARATION OF (AC) WHERE $R^2$ IS LOWER ALKYL

The compounds of Formula (II) are prepared from the intermediates of Formula (AC), where $R^2$ is lower alkyl, the preparation of which is shown below in Reaction Scheme IV.

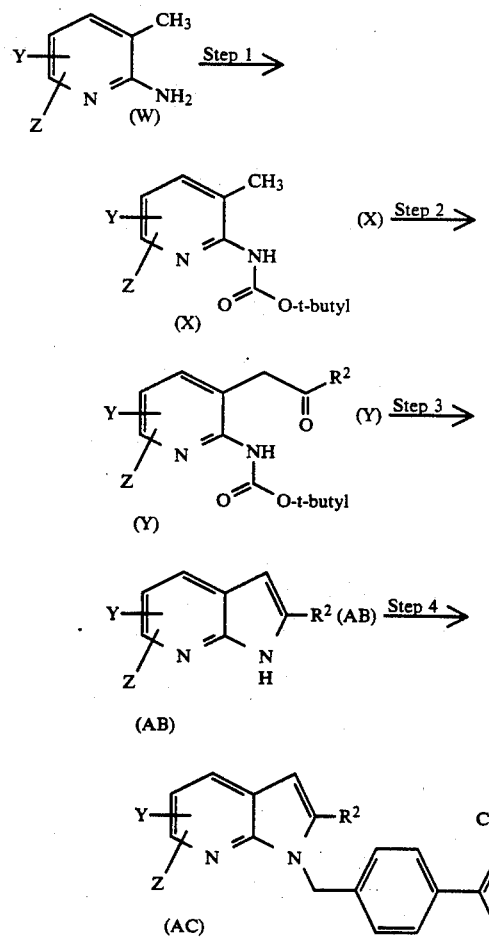

Starting Materials

The 2-amino-3-methylpyridine derivatives of Formula (W) are commercially available, for example from Aldrich. Alternatively, as is well known in the art, acid, ester, alkoxy, alkyl and halo substituted 2-amino-3-methylpyridine compounds of Formula (W) can be prepared by conventional means from commercially available substituted pyridines, e.g., by halogenation, nucleophilic substitution, etc.

Preparation of Compounds of Formula (X)

To prepare a compound of Formula (X), a compound of Formula (W) is reacted with about 1–2 molar equivalents, preferably about 1 molar equivalent, of di-t-butyl-dicarbonate in an inert solvent (such as ether, dichloromethane, or tetrahydrofuran, preferably tetrahydrofuran). The reaction is carried out at a temperature of about 60° C. to 100° C., preferably at about 80° C., for about 5 to 30 hours, preferably about 12 hours. When the reaction is substantially complete the t-butylcarbamate derivative of Formula (X) is isolated and purified by conventional means, preferably recrystallization.

Preparation of Compounds of Formula (Y)

To prepare a compound of Formula (Y), where $R^2$ is lower alkyl, a compound of Formula (X) is first reacted with about 2 molar equivalents of a strong base (such as a butyllithium, preferably sec-butyllithium), in an ethereal solvent (such as diglyme, ether, or tetrahydrofuran, preferably tetrahydrofuran), at a temperature of about −30° C. to −70° C., preferably at about −50° C., for about 1–60 minutes, preferably about 10 minutes.

To the lithium dianion thus formed is added about 1 to 1.5 molar equivalents, preferably about 1.1 molar equivalents, of an N-methoxy-N-methyl(lower-alkyl)amide of the formula $R^2C(O)N(OCH_3)CH_3$, in an ethereal solvent, preferably tetrahydrofuran, maintaining the temperature at about −80° C. to −50° C., preferably at about −60° C., for about 5 minutes to 1 hour, preferably about 10 minutes. When the reaction is substantially complete the t-butylcarboxyazaindole of Formula (Y) is isolated and purified by conventional means, preferably recrystallization.

Preparation of Compounds of Formula (AB)

To prepare a compound of Formula (AB), where $R^2$ is lower alkyl, a compound of Formula (Y) is dissolved in an inert aprotic solvent (such as ether, tetrahydrofuran, or methylene chloride; preferably methylene chloride), and about 0.1 to 2 molar equivalents, preferably about 1 molar equivalent, of trifluoroacetic acid is added. The reaction is carried out at about room temperature, for about 4–48 hours, preferably about 16 hours. When the reaction is substantially complete the azaindole of Formula (AB) is isolated by conventional means, preferably chromatography.

Preparation of Compounds of Formula (AC)

To prepare a compound of Formula (AC) where $R^2$ is lower alkyl, a compound of Formula (AB) where $R^2$ is lower alkyl is reacted with about 1 molar equivalent of an alkali metal hydride, preferably sodium hydride, at 10° C. to 40° C., preferably about 20° C. The reaction is carried out in a polar solvent, (such as tetrahydrofuran, DMSO, or DMF, preferably DMF), for about 5 minutes to 2 hours, preferably about 20 minutes. The anion thus formed is then reacted with about 1 to 1.5 molar equivalents, preferably about 1.2 molar equivalents, of a 4-halomethyl-2′-cyanobiphenyl compound or 4-tosylmethyl-2′-cyanobiphenyl, allowing the temperature to rise to about 20° C. When the reaction is substantially complete, the azaindole derivative of Formula (AC) where $R^2$ is lower alkyl is isolated and purified by conventional means, preferably chromatography.

5. PREPARATION OF (AI) AND (AJ) WHERE $R^2$ IS LOWER ALKYL

The compounds of Formula (III) are prepared from the intermediates of Formula (AI) and (AJ), where $R^2$ is lower alkyl, the preparation of which are shown below in Reaction Scheme V.

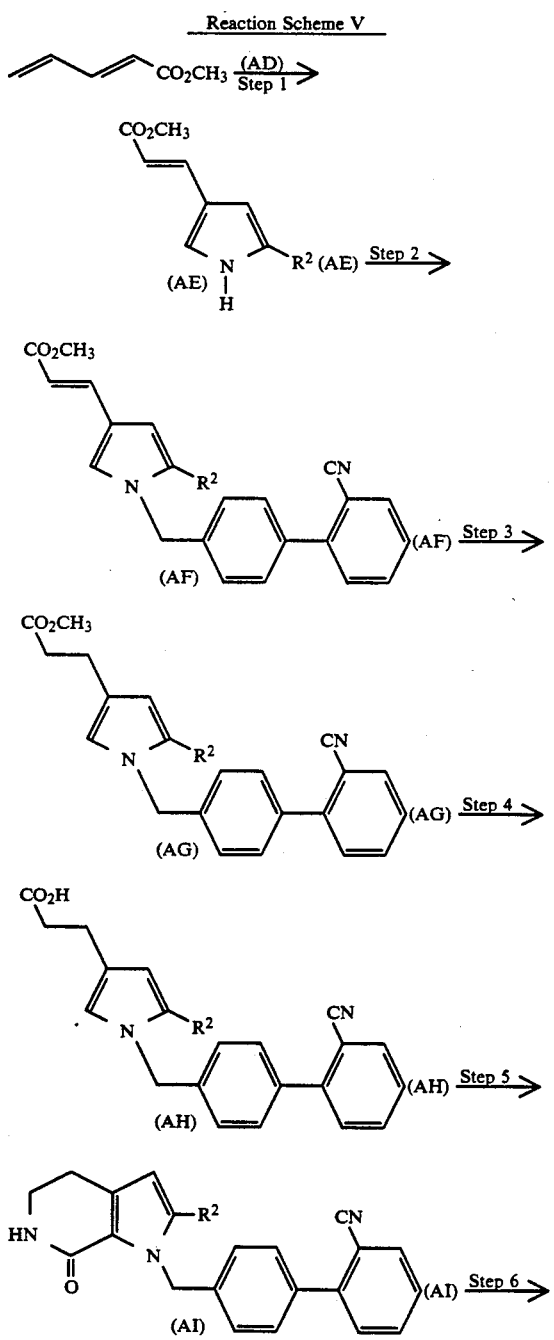

-continued
Reaction Scheme V

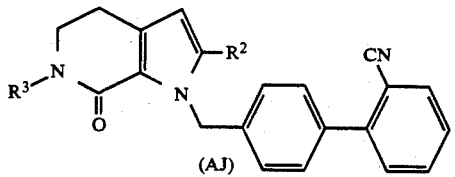

Starting Materials

In step 1, the compounds of Formula (AD), where $R^2$ is lower alkyl, are 1-tosylmethylisocyanide derivatives of the formula:

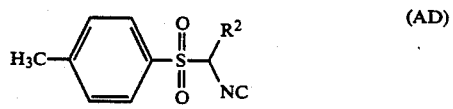

Such compounds are commercially available, for example from Aldrich. Alternatively, as is well known in the art, the compounds of Formula (AD) can be prepared by conventional means from 1-tosylmethyisocyanate, as described in van Leusen and Possel, *Tet. Lett.* 1975:3487–3488 (1975).

Preparation of Compounds of Formula (AE)

To prepare a compound of Formula (AE) where $R^2$ is lower alkyl, methylbutadiene-1-carboxylate is reacted with about 1–1.5 molar equivalents, preferably about 1.1 molecular equivalents, of an optionally substituted 1-tosylmethylisocyanide of Formula (AD), and about 1–1.5 molar equivalents, preferably about 1.1 molecular equivalents, an alkali metal hydride, preferably sodium hydride. The reaction is carried out in an organic solvent mixture (such as tetrahydrofuran, DME, and/or dry DMSO and anhydrous ether, preferably a mixture of dry DMSO and anhydrous ether), initially at a temperature about 0° C. for about 1 hour, and then at 10°–40° C., preferably about 20° C., for about 2–12 hours, preferably about 6 hours. When the reaction is substantially complete, the pyrrole derivative of Formula (AE) where $R^2$ is lower alkyl is isolated and purified by conventional means, preferably chromatography.

Preparation of Compounds of Formula (AF)

To prepare a compound of Formula (AF) where $R^2$ is lower alkyl, a compound of Formula (AE) where $R^2$ is lower alkyl is reacted with about 1–2 molar equivalents, preferably about 1.5 molar equivalents, of an alkali metal hydride, preferably sodium hydride, at $-10°$ C. to 20° C., preferably about 0° C. The reaction is carried out in a polar solvent, (such as tetrahydrofuran, DMSO, or DMF, preferably DMF), for about 10 minutes to 2 hours, preferably about 30 minutes. The anion thus formed is then reacted with about 1 to 1.5 molar equivalents, preferably about 1.2 molar equivalents, of a 4-halomethyl-2′-cyanobiphenyl compound or 4-tosylmethyl-2′-cyanobiphenyl, allowing the temperature to rise to about 20° C. When the reaction is substantially complete, the pyrrole derivative of Formula (AF) where $R^2$ is lower alkyl is isolated and purified by conventional means, preferably chromatography.

Preparation of Compounds of Formula (AG)

To prepare a compound of Formula (AG) where $R^2$ is lower alkyl, a compound of Formula (AF) where $R^2$ is lower alkyl is hydrogenated in the presence of a transition metal catalyst. The reaction is carried out in a polar solvent (such as ethyl acetate, methanol, or ethanol, preferably ethanol) under hydrogen, in the presence of a transition metal catalyst (such as di[triphenylphosphine]palladium chloride, palladium on carbon, or tetrakis[triphenylphosphine]palladium, preferably palladium on carbon), at about room temperature for about 2 to 16 hours, preferably about 4 hours. When the reaction is substantially complete, the pyrrole derivative of Formula (AG) where $R^2$ is lower alkyl is isolated and purified by conventional means.

Preparation of Compounds of Formula (AH)

To prepare a compound of Formula (AH), a compound of Formula (AG) is reacted with an excess of a base (such as potassium hydroxide, ammonium hydroxide, or sodium hydroxide; preferably sodium hydroxide) in water and an organic solvent (such as methanol, propanol, or ethanol; preferably methanol), at a temperature of about 50° C. to reflux, preferably at about reflux, for 2 to 10 hours, preferably about 4 hours. When the reaction is substantially complete the pyrrole derivative of Formula (AH) is isolated by conventional means.

Preparation of Compounds of Formula (AI)

To prepare a compounds of Formula (AI) where $R^2$ is lower alkyl, a compound of Formula (AH) is reacted with about 1–2 molar equivalents, preferably about 1.5 molar equivalents, of ethyl chloroformate, in the presence of 1–10 molar equivalents, preferably about 1.5 molar equivalents, of a tertiary amine, preferably triethylamine. The reaction is carried out in a solvent mixture of water and a water-miscible organic solvent (such as tetrahydrofuran, methylethyl ketone, or acetone, preferably acetone), for about 30 minutes to 4 hours, preferably about 1 hour, at a temperature of about $-10°$ C. to 20° C., preferably at about 0° C. The reaction mixture is then reacted with 1–3 molar equivalents, preferably about 1.5 molar equivalents, of an alkali metal azide (such as lithium azide, potassium azide or sodium azide, preferably sodium azide), for about 30 minutes to 4 hours, preferably about 1 hour, preferably maintaining the temperature at about 0° C. When the reaction is substantially complete, the product is isolated by conventional means, and dissolved in an organic solvent (such as benzene, xylene, or toluene, preferably toluene) and heated for 30 minutes to 2 hours, preferably about 1 hour, at 60 to 120° C., preferably about 100° C. When the reaction is substantially complete, the product is isolated by conventional means, and reacted with an excess of a Lewis acid (such as titanium tetrachloride, aluminum trichloride or boron trifluoride-diethylether complex, preferably boron trifluoridediethylether complex) in an organic solvent (such as tetrahydrofuran, DME or anhydrous ether, preferably anhydrous ether), for about 30 minutes to 4 hours, preferably about 2 hour, at a temperature of 0°–30° C., preferably about 10° C. When the reaction is substantially complete the tetrahydro-1H-pyrrolo[2,3-c]pyridin-7-one of Formula (AI) is isolated by conventional means, preferably crystallization.

Preparation of Compounds of Formula (AJ)

To prepare a compounds of Formula (AJ) where $R^2$ is lower alkyl, a compound of Formula (AI) is first reacted with about 1–1.5 molar equivalents, preferably about 1.1 molar equivalents, of an alkyl lithium base, preferably n-butyllithium, in an ethereal solvent (such as ether, monoglyme, or tetrahydrofuran; preferably tetrahydrofuran). The reaction is carried out at a temperature of $-100°$ C. to $-50°$ C., preferably about $-70°$ C., for about 5 minutes to 1 hour, preferably about 15 minutes. The anion thus formed is then reacted with about 1 to 2 molar equivalents, preferably about 1.5 molar equivalents, of an alkyl halide of formula $R^3$Hal, where Hal is chloride, bromide or iodide, preferably iodide, and allowed to warm to about room temperature. The reaction is continued for 4–30 hours, preferably about 16 hours. When the reaction is substantially complete the substituted tetrahydro-1H-pyrrolo[2,3-c]pyridin-7-one of Formula (AJ), where $R^2$ is lower alkyl, is isolated by conventional means, preferably chromatography.

PREPARATION OF COMPOUNDS OF FORMULA (I), (II) AND (III)

The preparation of the compounds of Formula (I), (II) and (III) is shown in Reaction Schemes VI, VII, VIII and IX below. It should be understood that the various substituents defined as X can be introduced into the ring (as shown in Reaction Schemes I to V) before conversion of the cyano group to the tetrazole, or alternatively after such conversion. Additionally, compounds where X is $-CO_2H$ can be converted to compounds where X is, for example, $-CO_2R^4$, $-CONR^5R^6$, etc, at any stage of the syntheses.

PREPARATION OF COMPOUNDS OF FORMULA (I)

A. Preparation of (I) where $R^1$ is Lower Alkyl and $R^2$ is 2''-(1H-tetrazol-5-yl)biphenyl-4'-ylmethyl The compounds of Formula (I) where $R^1$ is lower alkyl and $R^2$ is 2''-(1H-tetrazol-5-yl)biphenyl-4'-ylmethyl, identified as Formula (Ia), are prepared from the intermediates of Formula (K) or (L), as shown below in Reaction Scheme VI.

Reaction Scheme VI (K) or (L) ⟶

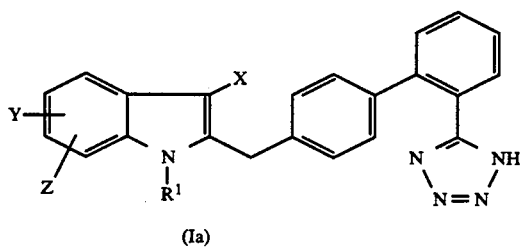

(Ia)

where $R^1$ is lower alkyl, and X, Y and Z are as defined in the Summary of the Invention.

Preparation of Compounds of Formula (Ia)

To prepare a compound of Formula (Ia), a compound of Formula (K) or Formula (L) is reacted with about 1–10 molar equivalents, preferably about 5 molar equivalents, of a trialkyl tin azide, preferably tributyltin azide, in an inert solvent (such as hexane, benzene, or xylene, preferably xylene). The reaction is carried out at a temperature of $80°-150°$ C., preferably at about reflux temperature, for about 8–48 hours, preferably about 20 hours. The mixture is then cooled to about $0°$ C., and an acid (such as potassium fluoridetetrafluoroboric acid/diethyl ether complex, sulfuric acid, or hydrochloric acid, preferably hydrochloric acid or potassium fluoride-tetrafluoroboric acid/diethyl ether complex) is added, and stirred for an additional 5–60 minutes, preferably about 15 minutes. When the reaction is substantially complete the indole of Formula (Ia) is isolated and purified by conventional means.

Preparation of Compounds of Formula (Ia) where X is $-CO_2R^4$, where $R^4$ is lower alkyl Compounds of Formula (Ia) where X is $-CO_2R^4$, where $R^4$ is lower alkyl, may be prepared from compounds of Formula (Ia) where X is $-CO_2H$ by methods well known in the art. For example, conversion of the $-CO_2H$ group to an acid chloride or carbonylimidazole followed by treatment with an alcohol of formula $R^4OH$, or by reaction of a compound of Formula (Ia) where X is $-CO_2H$ with an alcohol of formula $R^4OH$ in the presence of an acid catalyst, and the like.

Preparation of Compounds of Formula (Ia) where X is $-CONR^5R^6$

Compounds of Formula (Ia) where X is $-CONR^5R^6$, where $R^5$ and $R^6$ are as defined in the Summary of the Invention, are prepared by first reacting compounds of Formula (Ia) where X is $-CO_2H$ with about 1–1.5 molar equivalents, preferably about 1.2 molar equivalents, of an agent such as carbonyldipyrrole, carbonyldipyridine, or carbonyldiimidazole, preferably carbonyldiimidazole. The reaction is carried out in an inert solvent (such as ether, methylene chloride, or acetonitrile, preferably acetonitrile), at a temperature of $20°-50°$ C., preferably at reflux temperature, for 30 minutes to 2 hours, preferably about 1 hour. When the reaction is substantially complete, the reaction mixture is further treated with about 2–4 molar equivalents, preferably about 2.2 molar equivalents, of an amine of the formula $R^5R^6H$, where $R^5$ and $R^6$ are as defined above, and an excess of a tertiary amine (such as triisopropyl amine, pyridine or triethylamine, preferably triethylamine), maintaining the temperature at $20°-50°$ C., preferably at reflux temperature, for 6–30 hours, preferably about 16 hours. The mixture is then acidified (with, for example, acetic acid, sulfuric acid, or hydrochloric acid, preferably hydrochloric acid). When the reaction is substantially complete the 3-carboxamidoindole of Formula (Ia), where X is $-CONR^5R^6$, where $R^5$ and $R^6$ are as defined above, is isolated and purified by conventional means.

B. Preparation of (I) where $R^1$ is 2''-(1H-tetrazol-5-yl)biphenyl-4'-ylmethyl and $R^2$ is Lower Alkyl The compounds of Formula (I) where $R^1$ is 2''-(1H-tetrazol-5-yl)biphenyl-4'-ylmethyl and $R^2$ is lower alkyl, identified as Formula (Ib), are prepared from the intermediates of Formula (R) or (V), as shown below in Reaction Scheme VII.

Reaction Scheme VII (R) or (V) ⟶

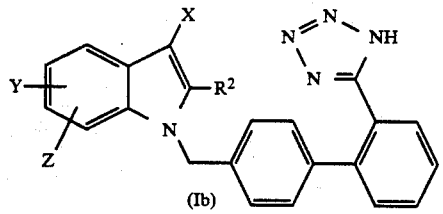

(Ib)

Preparation of Compounds of Formula (Ib)

To prepare a compound of Formula (Ib), a compound of Formula (R) or (V), where $R^2$ is lower alkyl, is reacted with a trialkyl tin azide, preferably tributyltin azide, as described above in Reaction Scheme VI. When the reaction is substantially complete the indole of Formula (Ib) is isolated and purified by conventional means.

Compounds of Formula (Ib) where X and Y are both $-CO_2R^4$, where $R^4$ is lower alkyl, can be prepared by the above procedure. Conventional base hydrolysis of these compounds gives compounds of Formula (Ib) where X and Y are both $-CO_2H$. Heating of the dicarboxylic compounds at about their melting T point gives compounds where X is hydrogen and Y is $-CO_2H$.

PREPARATION OF COMPOUNDS OF FORMULA (II)

A. Preparation of (II) where $R^1$ is 2"-(1H-tetrazol-5-yl)biphenyl-4'-ylmethyl and $R^2$ is Lower Alkyl The compounds of Formula (II) where $R^1$ is 2"-(1H-tetrazol-5-yl)biphenyl-4'-ylmethyl and $R^2$ is lower alkyl are prepared from the intermediates of Formula (AC), as shown below in Reaction Scheme VIII.

Reaction Scheme VIII (AC) ⟶

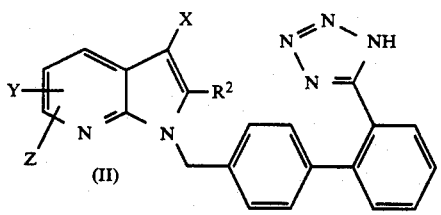

(II)

where $R^2$ is lower alkyl.

Preparation of (II) Where $R^2$ is Lower Alkyl

To prepare a compound of Formula (II) where $R^2$ is lower alkyl, a compound of Formula (AC), where $R^2$ is lower alkyl, is reacted with a trialkyl tin azide, preferably tributyltin azide, as described above in Reaction Scheme VI. The reaction mixture is then preferably acidified with potassium fluoride-tetrafluoroboric acid/diethyl ether complex, and stirred for about 8–24 hours, preferably about 12 hours. When the reaction is substantially complete the azaindole of Formula (II) is isolated and purified by conventional means, preferably chromatography.

Preparation of (II) where $R^2$ is lower alkyl and X is $-CO_2R^4$ or $-CONR^5R^6$ To prepare a compound of Formula (II) where $R^2$ is lower alkyl and X is $-CO_2R^4$ or $-CONR^5R^6$, a compound of Formula (II) where $R^2$ is lower alkyl and X is hydrogen is first reacted with phosgene as described above in Reaction Scheme I to give a compound of Formula (II) where X is $-CO_2H$. This compound is then converted to compounds where X is $-CO_2R^4$ or $-CONR^5R^6$ as described above.

B. Preparation of (II) where $R^1$ is Lower Alkyl and $R^2$ is 2"-(1H-tetrazol-5-yl)biphenyl-4'-ylmethyl The compounds of Formula (II) where $R^1$ is lower alkyl and $R^2$ is 2"-(1H-tetrazol-5-yl)biphenyl-4'-ylmethyl, may be prepared as shown in Reaction Scheme I, replacing the phenyl compounds of Formula (B) by appropriately substituted pyridine compounds.

PREPARATION OF COMPOUNDS OF FORMULA (III)

Preparation of (III) where $R^1$ is 2"-(1H-tetrazol-5-yl)biphenyl-4'-ylmethyl and $R^2$ is Lower Alkyl The compounds of Formula (III) where $R^1$ is 2"-(1H-tetrazol-5-yl)biphenyl-4'-ylmethyl and $R^2$ is lower alkyl may be prepared from the intermediates of Formula (AI) or (AJ), as shown below in Reaction Scheme IX.

Reaction Scheme IX (AI) or (AJ) ⟶

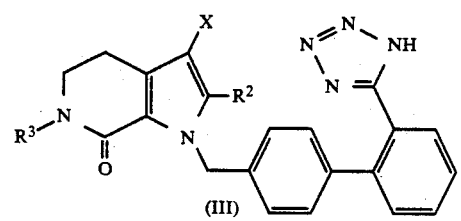

(III)

where $R^2$ is lower alkyl.

Preparation of (III) where $R^2$ is lower alkyl

To prepare a compound of Formula (III) where $R^2$ is lower alkyl, a compound of Formula (AI) or (AJ), where $R^2$ is lower alkyl, is reacted with a trialkyl tin azide, preferably tributyltin azide, as described above in Reaction Scheme VI. The reaction mixture is then preferably acidified with potassium fluoride-tetrafluoroboric acid/diethyl ether complex, and stirred for about 8–24 hours, preferably about 12 hours. When the reaction is substantially complete the tetrahydro-1H-pyrrolo[2,3-c]pyridin-7-one of Formula (III) is isolated and purified by conventional means, preferably chromatography.

Preparation of (III) where $R^2$ is lower alkyl and X is $-CO_2R^4$ or $-CONR^5R^6$ To prepare a compound of Formula (III) where $R^2$ is lower alkyl and X is $-CO_2R^4$ or $-CONR^5R^6$, a compound of Formula (III) where $R^2$ is lower alkyl and X is hydrogen is first reacted with phosgene as described above in Reaction Scheme I to give a compound of Formula (III) where X is $-CO_2H$. This compound is then converted to compounds where X is —$CO_2R^4$ or —$CONR^5R^6$ as described above.

B. Preparation of (III) where R is Lower Alkyl and $R^2$ is 2''-(1H-tetrazol-5-yl)biphenyl-4'-ylmethyl The compounds of Formula (III) where $R^1$ is lower alkyl and $R^2$ is 2''-(1H-tetrazol-5-yl)biphenyl-4'-ylmethyl, may be prepared as shown in Reaction Scheme I, replacing the phenyl compounds of Formula (B) by appropriately substituted tetrahydropyridin-2-one compounds.

Preparation of Compounds of Formula (I), (II) or (III) where X is lower alkyl

The preparation of compounds of Formula (I), (II) or (III) where X is lower alkyl may be accomplished by appropriately modifying the starting materials of the above Reaction Schemes. For example, starting with the compound of Formula (O), substituted by lower alkyl at the 1-position of the keto sidechain, and following the procedures of Reaction Schemes III and VII, a compound of Formula (I) where X is lower alkyl is obtained.

Likewise, starting with the compound of Formula (W) substituted by lower alkyl at the 3-position of the ring, and following the procedures of Reaction Schemes IV and VIII, a compound of Formula (II) where X is lower alkyl is obtained.

Likewise, starting with the compound of Formula (AE) substituted by lower alkyl at the 3-position of the ring, and following the procedures of Reaction Schemes V and IX, a compound of Formula (III) where X is lower alkyl is obtained.

Preparation of Compounds of Formula (I), (II) or (III) where X is halo

The preparation of compounds of Formula (I), (II) or (III) where X is halo may be accomplished by halogenating an appropriate intermediate in the above Reaction Schemes. For example, reacting a compound of Formula (P) with N-chlorosuccinimide gives compound (P) substituted at the 3-position by chlorine. Following the procedures of Reaction Schemes II and VI, compounds of Formula (I) where X is chloro are obtained. Similarly, reacting a compound of Formula (V) with N-chlorosuccinimide gives compound (V) substituted at the 3-position by chlorine. Following the procedures of Reaction Schemes III and VII, compounds of Formula (I) where X is chloro are obtained.

Similarly, other compounds of Formula (I), (II) and (III) where X is halo are obtained.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

Salts of Compounds of Formula (I), (II) and (II)

The compounds of Formula (I), (II) and (III) may be converted to a corresponding base addition salt by virtue of the presence of the acidic tetrazole group, and in some instances because of the presence of a carboxyl group. Such salts may be prepared from either inorganic or organic bases. Salts derived from inorganic bases include, but are not limited to, the sodium, potassium, lithium, ammonium, calcium, magnesium, ferrous, zinc, copper, manganous, aluminum, ferric, and manganic salts, and the like. Salts derived from organic bases include, but are not limited to, salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like.

The conversion is preferably accomplished by treatment of the free compound in an inert organic solvent with a stoichiometric amount of an appropriate base in an inert organic solvent (such as methanol or ethanol, preferably methanol) at a temperature of about 0°–50° C., preferably ambient temperature. The resulting salt may be brought out of solution with a less polar solvent, by lyophilization of the solution, or by simply evaporating the solvent.

The compounds of Formula (II) may be converted to a corresponding acid addition salt by virtue of the presence of a tertiary nitrogen atom. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

In summary, the compounds of the present invention are made by the procedures outlined below:

1. A process for preparing compounds of the Formula (I), wherein:
$R^1$ is lower alkyl;
$R^2$ is 2''-(1H-tetrazol-5-yl)biphenyl-4'-ylmethyl;
X is hydrogen, lower alkyl, halogen, —C(O)CF$_3$, —$CO_2R^4$, or —C(O)NR$^5$R$^6$;
Y is hydrogen, lower alkyl, lower alkoxy, hydroxy, halogen, or —$CO_2R^4$;
Z is hydrogen, lower alkyl, lower alkoxy, or halogen; wherein
$R^4$ is hydrogen or lower alkyl;
$R^5$ is hydrogen or lower alkyl;
$R^6$ is hydrogen or lower alkyl; or
$R^5$ and $R^6$ taken together with the nitrogen to which they are attached represent a heterocycle;
comprises:

reacting a compound of the formula:

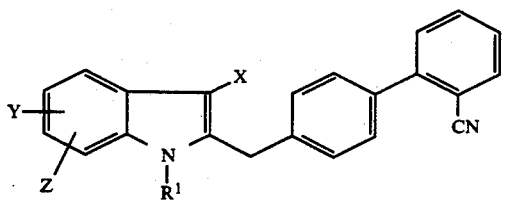

(K) or (L)

where $R^1$ is lower alkyl, and X, Y and Z are as defined in the Summary of the Invention;
with a trialkyl tin azide followed by treatment with an acid.

2. A process for preparing compounds of the Formula (I), wherein:
$R^1$ is 2''-(1H-tetrazol-5-yl)biphenyl-4'-ylmethyl;
$R^2$ is lower alkyl;
X is hydrogen, lower alkyl, halogen, —C(O)CF$_3$, —CO$_2$R$^4$, or —C(O)NR$^5$R$^6$;
Y is hydrogen, lower alkyl, lower alkoxy, hydroxy, halogen, or —CO$_2$R$^4$;
Z is hydrogen, lower alkyl, lower alkoxy, or halogen; wherein
$R^4$ is hydrogen or lower alkyl;
$R^5$ is hydrogen or lower alkyl;
$R^6$ is hydrogen or lower alkyl; or
$R^5$ and $R^6$ taken together with the nitrogen to which they are attached represent a heterocycle;
comprises:
reacting a compound of the formula:

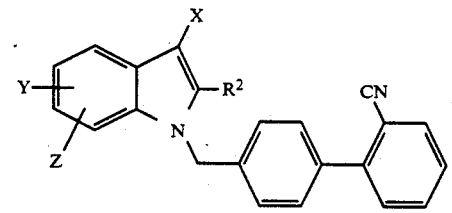

(R) or (V)

where $R^2$ is lower alkyl, and X, Y and Z are as defined in the Summary of the Invention;
with a trialkyl tin azide followed by treatment with an acid.

3. A process for preparing compounds of the Formula (II), wherein:
$R^1$ is 2''-(1H-tetrazol-5-yl)biphenyl-4'-ylmethyl;
$R^2$ is lower alkyl;
X is hydrogen, lower alkyl, halogen, —C(O)CF$_3$, —CO$_2$R$^4$, or —C(O)NR$^5$R$^6$;
Y is hydrogen, lower alkyl, lower alkoxy, hydroxy, halogen, or —CO$_2$R$^4$;
Z is hydrogen, lower alkyl, lower alkoxy, or halogen; with the proviso that Y and Z cannot be attached to the nitrogen atom;
wherein
$R^4$ is hydrogen or lower alkyl;
$R^5$ is hydrogen or lower alkyl;
$R^6$ is hydrogen or lower alkyl; or
$R^5$ and $R^6$ taken together with the nitrogen to which they are attached represent a heterocycle;
comprises:

reacting a compound of the formula:

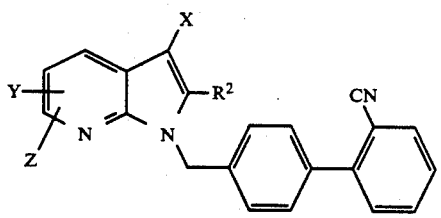

where $R^2$ is lower alkyl and X, Y and Z are as defined in the Summary of the Invention;
with a trialkyl tin azide followed by treatment with an acid.

4. A process for preparing compounds of the Formula (III), wherein:
$R^1$ is 2''-(1H-tetrazol-5-yl)biphenyl-4'-ylmethyl;
$R^2$ is lower alkyl;
X is hydrogen, lower alkyl, halogen, —C(O)CF$_3$, —CO$_2$R$^4$, or —C(O)NR$^5$R$^6$;
Y is hydrogen, lower alkyl, lower alkoxy, hydroxy, halogen, or —CO$_2$R$^4$;
Z is hydrogen, lower alkyl, lower alkoxy, or halogen; wherein
$R^4$ is hydrogen or lower alkyl;
$R^5$ is hydrogen or lower alkyl;
$R^6$ is hydrogen or lower alkyl; or
$R^5$ and $R^6$ taken together with the nitrogen to which they are attached represent a heterocycle;
comprises:
reacting a compound of the formula:

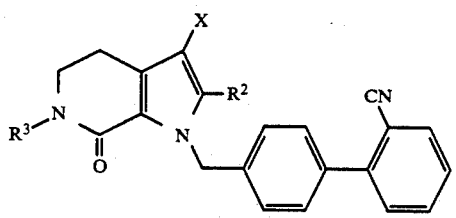

where $R^2$ is lower alkyl, $R^3$ is hydrogen or lower alkyl, and X is as defined in the Summary of the Invention;
with a trialkyl tin azide followed by treatment with an acid.

5. A process for preparing compounds of the Formula (I), (II) or (III), wherein:
$R^1$ and $R^2$ are different and are either lower alkyl or 2''-(1H-tetrazol-5-yl)biphenyl-4'-ylmethyl;
$R^3$ is hydrogen or lower alkyl;
X is —CO$_2$R$^4$ or —C(O)NR$^5$R$^6$;
Y is hydrogen, lower alkyl, lower alkoxy, hydroxy, halogen, or —CO$_2$R$^4$;
Z is hydrogen, lower alkyl, lower alkoxy, or halogen; wherein
$R^4$ is hydrogen or lower alkyl;
$R^5$ is hydrogen or lower alkyl;
$R^6$ is hydrogen or lower alkyl; or
$R^5$ and $R^6$ taken together with the nitrogen to which they are attached represent a heterocycle;
comprises:
reacting a compound of the formula:

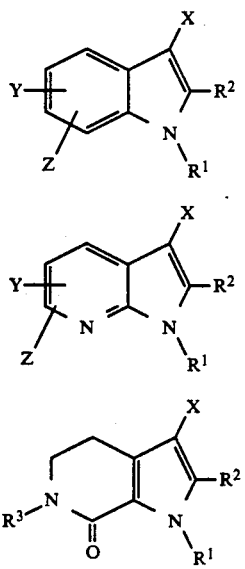

where X is hydrogen;
with phosgene, optionally followed by an alcohol of formula $R^4OH$, where $R^4$ is lower alkyl, or an amine of formula $R^5R^6NH$, where $R^5$ and $R^6$ are as defined in the Summary of the Invention.

6. Alternatively, a process for preparing compounds of the Formula (I), (II) or (III), wherein $R^1$, $R^2$, $R^3$, X, Y and Z are as defined in the Summary of the Invention, constitutes:

(a) reacting the compound of Formula (I), (II) or (III) with a base to give a pharmaceutically acceptable base addition salt; or (b) reacting a base addition salt of a compound of Formula (I), (II) or (III) with an acid to give the corresponding free acid; or (c) converting a base addition salt of a compound of Formula (I), (II) or (III) to another pharmaceutically acceptable base addition salt of Formula (I), (II) or (III).

UTILITY AND ADMINISTRATION

A. General Utility

The compounds of the present invention, and the pharmaceutically acceptable salts thereof, exhibit useful pharmacological properties in mammals, including use as cardiovascular agents, such as for treating hypertension, congestive heart failure, and chronic renal disease. In view of the local role of the renin angiotensin system in smooth muscle in the alimentary tract and in the brain, the compounds are also useful for treating disorders of the brain such as cognitive and affective disorders, including mood disorders, as well as disorders of the alimentary tract, including motility and secretory disorders and inflammatory bowel disease. The compounds of the present invention may also be used to treat chronic renal failure, glaucoma, as well as neuroblastoma and other growth disorders.

The ability of the compounds of Formulae (I), (II) and (III) to effectively inhibit the binding of angiotensin II to its receptors can be determined by a variety of in vitro and in vivo assays that are known to those of ordinary skill in the art. In particular, assays which inhibit the response of isolated smooth muscle and cardiac muscle to angiotensin II, and assays which inhibit hypertensive responses to angiotensin II in animal models are predictive of therapeutic utility.

B. Testing

In vitro assays for determining binding of the present compounds at angiotensin II receptors follow a method which is essentially that described by Gunther, *J. Biol. Chem.* 259:7622 (1984) and Whitebread et al., *Biochem. Biophys. Res. Comm.* 163:284 (1989). This method employs $[^{125}I]$-$Sar^1$ $Ile^8$ AII in membrane preparations from rat liver (AT-1 receptors) and bovine cerebellum (AT-2 receptors). Binding affinity of a test compound to angiotensin II receptor sites is thus demonstrated.

In vitro functional assays for determining antagonist activity of the present compounds at receptors for angiotensin follow a method which is essentially that described by Chiu et al, *J. Pharmacol. Exp. Ther.* 252:711 (1990) and Kamikawa et al., *Gastroenterology* 88:706 (1985). Isolated ring segments of rabbit thoracic aorta and isolated segments of guinea pig ileum are exposed to angiotensin II with and without test compounds, and a contractile response is evoked. Inhibition of contraction demonstrates angiotensin II receptor antagonist activity of the test compound.

In order to evaluate the in vivo anti-hypertensive activity of the present compounds, male normotensive rats are subjected to complete left renal artery ligation essentially as described by Wong et al., *J. Pharmacol. Exp. Ther.* 252:726–732 (1990), and a test compound is administered. Lowering of blood pressure demonstrates in vivo hypotensive activity of the test compound. In addition, in vivo testing can be conducted on conscious normotensive rats to which angiotensin II and a test compound are administered. In vivo activity is demonstrated by inhibition of the pressor response to angiotensin II by the test compound.

Cognition enhancing activity is determined using a modification of the Morris Water Maze spatial learning-memory assay (e.g., see Morris, R. M. G, *J. Neurosci. Methods* 1984, Vol. 11, pp 47–60). This procedure tests rats in six trials daily for two consecutive days, recording the time to find a hidden platform. The cognitive enhancement assay is described in Example 20.

C. General Administration

In applying the compounds of this invention to treatment of the above conditions, any pharmaceutically acceptable mode of administration can be used, either alone or in combination with other pharmaceutically acceptable excipients, including solid, semi-solid liquid or aerosol dosage forms, such as, for example, tablets, capsules, powders, liquids, suspensions, suppositories, aerosols or the like, or in sustained or controlled release dosage forms for the prolonged administration of the compound at a predetermined rate, preferably in unit dosage forms suitable for single administration of precise dosages. The compositions will typically include a conventional pharmaceutical carrier or excipient and an active compound of formula (I), (II) or (II) or the pharmaceutically acceptable salts thereof. In addition, these compositions may include other medicinal agents, pharmaceutical agents, carriers, adjuvants, etc., e.g. antihypertensive agents such as angiotensin converting enzyme (ACE) inhibitors, beta-blocking agents and diuretics; bronchodilating agents and antiasthmatics; steroids; antiinflammatories; and non-steroidal antiinflammatories (NSAIDs).

Generally, depending on the intended mode of administration, the pharmaceutically acceptable composition will contain about 0.1% to 90%, preferably about 0.5% to 50%, by weight of a pharmaceutically active compound of this invention, the remainder being suitable pharmaceutical excipients, carriers, etc.

The amount of active compound administered will, of course, be dependent on the subject and disease state being treated, the severity of the affliction, the manner of administration and the judgment of the prescribing physician. However, an effective dosage is int eh range of about 0.1 mg to about 100 mg/kg of body weight, preferably about 1 mg to 10 mg/kg. For an average 70 kg human, this would amount to about 7 mg to 7 g per day, or preferably 70-700 mg per day.

The preferred manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like.

Preferably the composition will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15the Edition, 1975.

The composition or formulation to be administered will, in any event, contain a quantity of the active compound(s) in an amount effective to alleviate the symptoms of the subject being treated.

Dosage forms or compositions containing active ingredient (compounds of formula (I), (II) or (III)) in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, glucose, sucrose, magnesium carbonate, and the like. Such compositions take the form of solutions, suspensions, tablets, capsules, powders, sustained release formulations and the like. Such compositions may contain 0.01%-95% active ingredient, preferably 0.1-50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing compounds of Formula (I), (II) or (III) or their salts in vegetable oils, glycols, triglycerides, propylene glycol esters (e.g. propylene carbibate) and the like, and encapsulating these solution or suspension in hard or soft gelatin capsule shells.

Other useful formulations include those set forth in U.S. Pat. Nos. 28,819 and 4,358,603.

The formulation can be administered in a single unit dosage form for continuous treatment or in a single unit dosage form ad libitum when relief of symptoms is specifically required.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2-2% of the active agent in solution.

Nasal administration is generally characterized by inhalation of the compounds of formula (I), (II) or (III) alone or in combination with other pharmaceutically acceptable excipients.

Formulations of compounds of formula (I), (II) or (II) may also be administered to the respiratory tract as an aerosol or solution for a nebulizer, or as a microfine powder for insufflation, alone or in combination with an inert carrier such as lactose, for the treatment of reversible airways obstruction and asthma. In such a case, the particles of the formulation have diameters of less than 50 microns, preferably less than 10 microns.

Pharmaceutical compositions suitable for the treatment of glaucoma may be prepared by mixing the active compound with a non-toxic pharmaceutical organic carrier, or with a pharmaceutically acceptable inorganic carrier. Typical of such pharmaceutically acceptable carriers are, for example, water, mixtures of water and water-miscible solvents such as lower alkanols or vegetable oils, glycerol, polyalkylene glycols, hydroxyethyl cellulose, ethyl oleate, carboxymethyl cellulose, polyvinylpyrrolidone, other polymers water miscible such as cellulose derivatives (methylcellulose, carboxymethylcellulose alkaline derivative, hydroxymethylcellulose, hydroxyethylcellulose) and other conventionally employed acceptable carriers. The pharmaceutical composition may also contain non-toxic auxiliary substances such as emulsifying, preserving, wetting, bodying agents and the like, as for example, polyethylene glycols 200, 300, 400, and 600; carbowaxes 1,000, 1,500, 4,000, 6,000 and 10,000; a polyanionic polymer, e.g. a carboxyvinylpolymer having a molecular weight of from about 4,000 to about 6,000,000; antibacterial components such as quaternary ammonium compounds, phenylmercuric salts known to have cold sterilizing properties and which are non-injurious in use; thimerosol, methyl and propylparaben, benzylic alcohol, phenylethanol; buffering ingredients and isotonic agents such as alkali metal chloride, borate, acetate, gluconate buffers; antioxidant agents such as sodium metabisulfite, butylated hydroxyanisole, butylated hydroxytoluene and other conventional ingredients such as sorbitan monolaurate, triethanolamine oleate, polyoxyethylene sorbitan monopalmitate, dioctyl alkali metal sulfosuccinate, monothioglycerol, ethylenediamine tetraacetic and the like.

EXAMPLES

The following preparations and examples are given to enable those skilled in the art to more clearly understand and practice the present invention. They should not be considered as a limitation on the scope of the invention, but merely as being illustrative and representative of the preferred embodiments of the present invention.

Unless specified to the contrary, these preparations and examples are carried out under an inert atmosphere, for example nitrogen or argon.

PREPARATION 1

Preparation of Compounds of Formula (B)

A. Preparation of (B) where Y and Z are hydrogen

A solution of o-toluidine (25 g), di-t-butyldicarbonate (56 g) in tetrahydrofuran (250 ml) was refluxed for 4 hours. The reaction mixture was poured onto ice water/dilute sodium bicarbonate solution and extracted twice with ether. The organic layer was then washed with brine and dried over magnesium sulfate. The solvent was evaporated under reduced pressure; crystallization of the residue from hexane gave 2-methylphenyl-t-butylcarbamate (42 g), a compound of Formula (B), m.p. 82°-83° C.

B. Preparation of (B), varying Y and Z

Similarly, following the procedures of Preparation 1A above, but replacing o-toluidine with:
3-methoxy-2-methylaniline;
2,4-dimethylmethylaniline;
5-hydroxy-2-methylaniline;
6-fluoro-2-methylaniline; and
6-chloro-2,4-dimethylaniline; the following exemplary intermediates of Formula (B) are prepared:
3-methoxy-2-methylphenyl-t-butylcarbamate;
4-methoxy-2-methylphenyl-t-butylcarbamate;
2,4-dimethylphenyl-t-butylcarbamate;
5-hydroxy-2-methylphenyl-t-butylcarbamate;
6-fluoro-2-methylphenyl-t-butylcarbamate; and
6-chloro-2,4-dimethylphenyl-t-butylcarbamate.

PREPARATION 2

Preparation of Compounds of Formula (F)

A. Preparation of (F) where Y and Z are hydrogen

A solution of 2-methylphenyl-t-butylcarbamate (5.0 g), prepared, for example, as described in Preparation 1, in tetrahydrofuran (100 ml) was cooled to −40° C. under argon. s-Butyllithium (37 ml) was added dropwise, maintaining the temperature at −45° to −35° C. After addition of the s-butyllithium, the temperature of the mixture was lowered to −75° C., producing an orange solution.

A solution of N-methyl-N-methoxy-p-bromophenylacetylamide (5.8 g) (Formula (E), prepared, e.g. as described in Reaction Scheme I, in tetrahydrofuran (50 ml) was then added dropwise, maintaining the temperature at below −65° C. After stirring for 10 minutes, the reaction was quenched with water and ether. The mixture was poured onto ice, extracted twice with ether, the organic layer dried over sodium sulphate, and the solvent evaporated to afford an oil. The oil was dissolved in methylene chloride (150 ml) and trifluoroacetic acid (5 ml) was added. The solution was stirred for 30 minutes at room temperature. The mixture was poured onto dilute sodium bicarbonate solution, extracted with ether, the organic layer dried over magnesium sulphate, and the solvent evaporated to produce an oil. The oil was further purified by silica gel chromatography eluting with 15% ethyl acetate in hexane, to give t-butyl 2-(p-bromophenylmethyl)indole-1-carboxylate (6.0 g), a compound of Formula (F), as an oil.

B. Preparation of (F), varying Y and Z

Similarly, following the procedures of Preparation 2A above, but replacing 2-methylphenyl-t-butylcarbamate with other compounds of Formula (B), the following exemplary intermediates of Formula (F) are prepared:
t-butyl 2-(p-bromophenylmethyl)-4-methoxyindole-1-carboxylate;
t-butyl 2-(p-bromophenylmethyl)-5-methoxyindole-1-carboxylate;
t-butyl 2-(p-bromophenylmethyl)-5-methylindole-1-carboxylate;
t-butyl 2-(p-bromophenylmethyl)-6-hydroxyindole-1-carboxylate
t-butyl 2-(p-bromophenylmethyl)-7-fluoroindole-1-carboxylate; and
t-butyl 2-(p-bromophenylmethyl)-7-chloro-5-methylindole-1-carboxylate.

PREPARATION 3

Preparation of Compounds of Formula (G)

A. Preparation of (G) where Y and Z are hydrogen

A mixture of t-butyl 2-(p-bromophenylmethyl)indole-1-carboxylate (F) (6.0 g) (prepared, e.g., as described in Preparation 2), 10% sodium hydroxide in water (20 ml), and ethanol (150 ml), was heated under reflux for 6 hours. The mixture was then poured onto a mixture of ice water/dilute brine and extracted twice with ethyl acetate. The extract was washed with brine and dried over magnesium sulphate. The solvent was evaporated under reduced pressure to produce an oil, which then crystallized. The material was recrystallized from methyl t-butyl ether to give 2-(p-bromophenylmethyl)indole (2.2 g), a compound of Formula (G), m.p. 136° C.

B. Preparation of (G), varying Y and Z

Similarly, following the procedures of Preparation 3A above, but replacing t-butyl 2-(p-bromophenylmethyl)indole-1-carboxylate with other compounds of Formula (F), the following exemplary intermediates of Formula (G) are prepared:

2-(p-bromophenylmethyl)-4-methoxyindole;
2-(p-bromophenylmethyl)-5-methoxyindole;
2-(p-bromophenylmethyl)-5-methylindole;
2-(p-bromophenylmethyl)-6-hydroxyindole;
2-(p-bromophenylmethyl)-7-fluoroindole; and
2-(p-bromophenylmethyl)-7-chloro-5-methylindole.

PREPARATION 4

Preparation of Compounds of Formula (H)

A. Preparation of (H) where $R^1$ is n-Butyl and Y and Z are Hydrogen

A mixture of sodium hydride (0.32 g) in DMF (50 ml) was cooled in an ice bath. A solution of 2-(p-bromophenylmethyl)-indole (2.0 g), prepared, e.g., as described in Preparation 3, in DMF, was added, and the mixture stirred for 10 minutes. 1-Iodobutane (0.9 ml) in DMF was added dropwise, and the mixture stirred for 30 minutes. It was then poured into cold dilute HCl and extracted with ether. The extract was washed three times with cold water, dried over magnesium sulphate, and the solvent evaporated to afford an orange-red oil, 1-(n-butyl)-2-(p-bromophenylmethyl)indole (2.5 g), a compound of Formula (H).

B. Preparation of (H), varying $R^1$, Y and Z

Similarly, following the procedures of Preparation 4A above, but optionally replacing 2-(p-bromophenylmethyl)indole with other compounds of Formula (G), and optionally replacing iodobutane with other lower alkyl halides, the following exemplary intermediates of Formula (H) are prepared:

1-ethyl-2-(p-bromophenylmethyl)indole;
1-(2-propyl)-2-(p-bromophenylmethyl)indole;
1-(n-hexyl)-2-(p-bromophenylmethyl)indole;
1-(n-butyl)-2-(p-bromophenylmethyl)-4-methoxyindole;
1-(n-butyl)-2-(p-bromophenylmethyl)-5-methoxyindole;
1-(n-butyl)-2-(p-bromophenylmethyl)-5-methylindole;
1-(n-butyl)-2-(p-bromophenylmethyl)-6-hydroxyindole;
1-(n-butyl)-2-(p-bromophenylmethyl)-7-fluoroindole; and
1-(n-butyl)-2-(p-bromophenylmethyl)-8-chloro-5-methylindole.

PREPARATION 5

Preparation of Compounds of Formula (J)

A. Preparation of (J) where $R^1$ is n-Butyl and Y and Z are Hydrogen

To a cold (−70° C.) stirring solution of 1-(n-butyl)-2-(p-bromophenylmethyl)indole (H) (10.0 g), prepared, e.g., as described in Preparation 4, in tetrahydrofuran (150 ml) was added dropwise n-butyl lithium (18 ml, 2.5 M), and stirring was continued for 15 minutes. Tributyl borate (12.5 ml) in tetrahydrofuran was then added dropwise and the reaction was allowed to warm to 0° C. It was then quenched with 10% HCl (60 ml) (pH 2–3) and stirred for 15 minutes at 20° C. The reaction mixture was extracted three times with ether, the extract washed with water, dried with magnesium sulfate, and the solvent was evaporated to produce an oil, 1-(n-butyl)-2-[4'-(dihydroxyboron)phenylmethyl]indole (7.8 g), a compound of Formula (J).

B. Preparation of (J), varying $R^1$, Y and Z

Similarly, following the procedures of Preparation 5A above, but replacing 1-(n-butyl)-2-(p-bromophenylmethyl)indole with other compounds of Formula (H), the following exemplary intermediates of Formula (J) are prepared:

1-ethyl-2-[4'-(dihydroxyboron)phenylmethyl]indole;
1-(2-propyl)-2-[4'-(dihydroxyboron)phenylmethyl]indole;
1-(n-hexyl)-2-[4'-(dihydroxyboron)phenylmethyl]indole;
1-(n-butyl)-2-[4'-(dihydroxyboron)phenylmethyl]-4-methoxyindole;
1-(n-butyl)-2-[4'-(dihydroxyboron)phenylmethyl]-5-methoxyindole;
1-(n-butyl)-2-[4'-(dihydroxyboron)phenylmethyl]-5-methylindole;
1-(n-butyl)-2-[4'-(dihydroxyboron)phenylmethyl]-6-hydroxyindole;
1-(n-butyl)-2-[4'-(dihydroxyboron)phenylmethyl]-7-fluoroindole; and
1-(n-butyl)-2-[4'-(dihydroxyboron)phenylmethyl]-7-chloro-5-methylindole.

PREPARATION 6

Preparation of Compounds of Formula (K)

A. Preparation of (K) where $R^1$ is n-Butyl and Y and Z are Hydrogen 1-(n-Butyl)-2-[4'-(dihydroxyboron)phenylmethyl]indole (J), (14.0 g), prepared, e.g., as described in Preparation 5, was dissolved in a mixture of toluene (200 ml), ethanol (40 ml) and 2M sodium carbonate (40 ml). To this mixture was added 1-cyano-2-bromobenzene (5.8 g) and tetrakis[triphenyl phosphine]palladium (0.6 g), and the combined mixture refluxed with vigorous stirring for 24 hours. The reaction mixture was then poured onto water and the layers separated. The organic layer was dried over magnesium sulphate, and the solvent removed under reduced pressure to afford an oil, which was further purified by silica gel chromatography eluting with 10% ethyl acetate in hexane, to yield 1-(n-butyl)-2-(2''-cyanobiphenyl-4'-ylmethyl)indole (8.1 g), a compound of Formula (K), m.p. 64°–68° C.

B. Preparation of (K), varying $R^1$, Y and Z

Similarly, following the procedures of Preparation 6A above, but replacing 1-(n-butyl)-2-[4'-(dihydroxyboron)phenylmethyl]indole with other compounds of Formula (J), the following exemplary intermediates of Formula (K) are prepared:

1-ethyl-2-(2''-cyanobiphenyl-4'-ylmethyl)indole;
1-(2-propyl)-2-(2''-cyanobiphenyl-4'-ylmethyl)indole;
1-(n-hexyl)-2-(2''-cyanobiphenyl-4'-ylmethyl)indole;
1-(n-butyl)-2-(2''-cyanobiphenyl-4'-ylmethyl)-4-methoxyindole;
1-(n-butyl)-2-(2''-cyanobiphenyl-4'-ylmethyl)-5-methoxyindole;
1-(n-butyl)-2-(2''-cyanobiphenyl-4'-ylmethyl)-5-methylindole;
1-(n-butyl)-2-(2''-cyanobiphenyl-4'-ylmethyl)-6-hydroxyindole;
1-(n-butyl)-2-(2''-cyanobiphenyl-4'-ylmethyl)-7-fluoroindole; and
1-(n-butyl)-2-(2''-cyanobiphenyl-4'-ylmethyl)-7-chloro-5-methylindole.

PREPARATION 7

Preparation of Compounds of Formula (L)

A. Preparation of (L) where $R^1$ is n-Butyl, X is —CO$_2$H, and Y and Z are Hydrogen To a solution of 1-(n-butyl)-2-(2''-cyanobiphenyl-4'-ylmethyl)indole (K) (5.0 g), prepared e.g., as described in Preparation 6, in tetrahydrofuran (100 ml) at 0° C. was added phosgene solution (10 ml, 20% in toluene) dropwise. The reaction was kept at 0° C. overnight. Water (20 ml) was then added and the mixture stirred for 20 minutes. The layers were separated, the aqueous phase extracted with ether, then the combined organic layers washed with dilute sodium hydroxide. The aqueous layer was acidified at 0° C. with dilute HCl, and the resultant precipitate was filtered off and washed with water and air dried, to yield 1-(n-butyl)-2-(2''-cyanobiphenyl-4'-ylmethyl)indole-3-carboxylic acid (2.4 g), a compound of Formula (L), m.p. 186°–188° C.

H. Preparation of (L) where $R^1$ is n-Butyl, X is —COCF$_3$, and Y and Z are Hydrogen To a solution of 1-(n-butyl)-2-(2''-cyanobiphenyl-4'-ylmethyl)indole (K) (0.9 g), prepared e.g., as described in Preparation 6, in dimethylformamide (20 ml) at 0° C. was added trifluoroacetic anhydride (0.4 ml) dropwise. The reaction was stirred for 10 minutes, and poured into ice/water. The precipitate was filtered off, washed with water, and recrystallized from ether/hexane, to give 1-(n-butyl)-2-(2''-cyanobiphenyl-4'-ylmethyl)-3-trifluoroacetylindole (0.85 g), a compound of Formula (L).

C. Preparation of (L), varying $R^1$, Y and Z

Similarly, following the procedures of Preparation 7A or 7B above, but replacing 1-(n-butyl)-2-(2''-cyanobiphenyl-4'-ylmethyl)indole with other compounds of Formula (K), the following exemplary intermediates of Formula (L) are prepared:

1-ethyl-2-(2''-cyanobiphenyl-4'-ylmethyl)indole-3-carboxylic acid;
1-(2-propyl)-2-(2''-cyanobiphenyl-4'-ylmethyl)indole-3-carboxylic acid;
1-(n-hexyl)-2-(2''-cyanobiphenyl-4'-ylmethyl)indole-3-carboxylic acid;
1-(n-butyl)-2-(2''-cyanobiphenyl-4'-ylmethyl)-4-methoxyindole-3-carboxylic acid;
1-(n-butyl)-2-(2''-cyanobiphenyl-4'-ylmethyl)-5-methoxyindole-3-carboxylic acid;
1-(n-butyl)-2-(2''-cyanobiphenyl-4'-ylmethyl)-5-methylindole-3-carboxylic acid;
1-(n-butyl)-2-(2''-cyanobiphenyl-4'-ylmethyl)-6-hydroxyindole-3-carboxylic acid;
1-(n-butyl)-2-(2''-cyanobiphenyl-4'-ylmethyl)-7-fluoroindole-3-carboxylic acid;
1-(n-butyl)-2-(2''-cyanobiphenyl-4'-ylmethyl)-3-trifluoroacetyl-7-fluoroindole; and
1-(n-butyl)-2-(2''-cyanobiphenyl-4'-ylmethyl)-7-chloro-5-methylindole-3-carboxylic acid.

PREPARATION 8

Preparation of Compounds of Formula (N)

A. Preparation of (N) where Y is 3-Methoxycarbonyl and Z is Hydrogen

A solution of methyl 3-methyl-2-nitrobenzoate (M) (51 g) in N,N-dimethylformamide dimethylacetal (100 ml) and DMF (250 ml) was refluxed for 72 hours. The mixture was allowed to cool to room temperature, and was poured into ice water. The precipitate was filtered off, affording 3-carboxymethyl-$\beta$-(N,N-dimethylamino)-2-nitrostyrene (34 g), a compound of Formula (N), m.p. 124°–126° C.

B. Preparation of (N) where Y is 4-Methoxycarbonyl and Z is Hydrogen

Similarly, following the procedures of Preparation 8A above, but replacing methyl 3-methyl-2-nitrobenzoate with methyl 4-methyl-3-nitrobenzoate, the following intermediate of Formula (N) was prepared:

4-carboxymethyl-$\beta$-(N,N-dimethylamino)-2-nitrostyrene, m.p. 126°–127° C.

C. Preparation of (N), varying Y and Z

Similarly, following the procedures of Preparation 8A above, but replacing methyl 3-methyl-2-nitrobenzoate with other compounds of Formula (M), the following exemplary intermediates of Formula (N) are prepared:

3-methoxy-$\beta$-(N,N-dimethylamino)-2-nitrostyrene;
4-fluoro-$\beta$-(N,N-dimethylamino)-2-nitrostyrene;
5-carboxymethyl-$\beta$-(N,N-dimethylamino)-2-nitrostyrene;
6-methyl-$\beta$-(N,N-dimethylamino)-2-nitrostyrene; and
4-chloro-3-methyl-$\beta$-(N,N-dimethylamino)-2-nitrostyrene.

PREPARATION 9

Preparation of Compounds of Formula (O)

A. Preparation of (O) where $R^2$ is n-Butyl, Y is 3-Methoxycarbonyl, and Z is Hydrogen A mixture of 3-carboxymethyl-$\beta$(N,N-dimethylamino)-2-nitrostyrene (N) (34 g) (prepared, e.g., as described in Preparation 8), valeryl chloride (19 ml), and pyridine (16 ml) in dichloromethane (400 ml) was refluxed for 24 hours. The mixture was allowed to cool to room temperature, washed twice with water, and solvent removed under reduced pressure. The residual dark oil was dissolved in dioxane (150 ml) and water (75 ml) and heated under reflux for 16 hours. The mixture was then cooled to room temperature, diluted with water and extracted with ether. The ether extract was washed with dilute HCl, followed by aqueous sodium bicarbonate and brine, dried over sodium sulfate and the solvent evaporated. Chromatography on silica gel, eluting with 20% ethyl acetate/hexane, afforded methyl 2-nitro-3-(hexan-2-one)benzoate (17.3 g), a compound of Formula (O), as an oil.

B. Preparation of (O) where $R^2$ is n-Butyl, Y is 4-Methoxycarbonyl and Z is Hydrogen Similarly, following the procedures of Preparation 9A above, but replacing 3-carboxymethyl-β(N,N-dimethylamino)-2-nitrostyrene with 4-carboxymethyl-β-(N,N-dimethylamino)-2-nitrostyrene, the following intermediate of Formula (O) was prepared:

methyl 3-nitro-4-(hexan-2-one)benzoate, m.p. 63°-64° C.

C. Preparation of (O), varying $R^2$, Y and Z

Similarly, following the procedures of Preparation 9A above, but optionally replacing 3-carboxymethyl-β(N,N-dimethylamino)-2-nitrostyrene with other compounds of Formula (N), and optionally replacing valeryl chloride with other lower acyl halides, the following exemplary intermediates of Formula (O) are prepared:

methyl 2-nitro-3-(butan-2-one)benzoate;
methyl 2-nitro-3-(pentan-2-one)benzoate;
methyl 2-nitro-3-(octan-2-one)benzoate;
1-(3-methoxy-2-nitrophenyl)hexan-2-one;
1-(4-fluoro-2-nitrophenyl)hexan-2-one;
1-(5-carboxymethyl-2-nitrophenyl)hexan-2-one;
1-(6-methyl-2-nitrophenyl)hexan-2-one; and
1-(4-chloro-3-methyl-2-nitrophenyl)hexan-2-one.

PREPARATION 10

Preparation of Compounds of Formula (P)

A. Preparation of (P) where $R^2$ is n-Butyl Y is 7-Methoxycarbonyl, and Z is Hydrogen A mixture of methyl 2-nitro-3-(hexan-2-one)benzoate (O) (17.3 g) (prepared, e.g., as described in Preparation 9), and zinc dust (50 g) in acetic acid (200 ml) was stirred at 90° C. for 16 hours. The mixture was filtered and the filtrate was diluted with water and extracted twice with ethyl acetate. The ethyl acetate extract was washed twice with water, then with aqueous sodium bicarbonate, and finally brine, dried over sodium sulfate and the solvent evaporated under reduced pressure. Chromatography of the residue on silica gel, eluting with 10% ethyl acetate/hexane, afforded methyl 2-(n-butyl)indole-7-carboxylate (11.5 g), a compound of Formula (P), as an oil.

B. Preparation of (P) where $R^2$ is n-Butyl, Y is 6-Methoxycarbonyl, and Z is Hydrogen Similarly, following the procedures of Preparation 10A above, but replacing methyl 2-nitro-3-(hexan-2-one)benzoate with methyl 3-nitro-4-(hexan-2-one)benzoate, the following intermediate of Formula (P) was prepared:

methyl 2-(n-butyl)indole-6-carboxylate, m.p. 76°-77° C.

C. Preparation of (P), varying $R^2$, Y and Z

Similarly, following the procedures of Preparation 10A above, but replacing methyl 2-nitro-3-(hexan-2-one)benzoate with other compounds of Formula (O), the following exemplary intermediates of Formula (P) are prepared:

methyl 2-ethylindole-7-carboxylate;
methyl 2-(n-propyl)indole-7-carboxylate;
methyl 2-(n-hexyl)indole-7-carboxylate;
2-(n-butyl)-7-methoxyindole;
2-(n-butyl)-6-fluoroindole;
methyl 2-(n-butyl)indole-5-carboxylate;
2-(n-butyl)-4-methylindole; and
2-(n-butyl)-6-chloro-7-methylindole.

PREPARATION 11

Preparation of Compounds of Formula (O)

A. Preparation of (O) where $R^2$ is n-Butyl, X is 3-Methoxycarbonyl, Y is 7-Methoxycarbonyl, and Z is Hydrogen A solution of phosgene in toluene (37 ml, 1.9M) was added to a solution of methyl 2-(n-butyl)indole-7-carboxylate (P) 11.5 g) (prepared, e.g., as described in Preparation 10), at 5° C. in dichloromethane (75 ml). The solution was stirred at room temperature for 16 hours, cooled in an ice bath, and treated with methanol (20 ml). Water was added, and the dichloromethane layer was separated and solvent evaporated under reduced pressure. Chromatography on silica gel, eluting with 20% ethyl acetate/hexane, afforded dimethyl 2-(n-butyl)indole-3,7-dicarboxylate (7.4 g), a compound of Formula (Q), as an oil.

B. Preparation of (O) where $R^2$ is n-Butyl, X is 3-Chloro, Y is 7-Methoxycarbonyl, and Z is Hydrogen To a solution of methyl 2-(n-butyl)indole-7-carboxylate (P) (0.3 g) in 6 ml of dimethylformamide at room temperature was added N-chlorosuccinimide (0.17 g). The solution was stirred at room temperature for 16 hours, then water was added, and the mixture extracted with ether. The extract was separated and solvent evaporated under reduced pressure, to give methyl 2-(n-butyl)-3-chloroindole-7-carboxylate, a compound of Formula (Q) where X is chloro, as an oil.

B. Preparation of (O), varying $R^2$, Y and Z

Similarly, following the procedures of Preparation 11A above, but optionally replacing methyl 2-(n-butyl)indole-7-carboxylate with other compounds of Formula (P), and optionally replacing phosgene with trifluoroacetic anhydride, the following exemplary intermediates of Formula (Q) are prepared:

dimethyl 2-ethylindole-3,7-dicarboxylate;
dimethyl 2-(n-propyl)indole-3,7-dicarboxylate;
dimethyl 2-(n-hexyl)indole-3,7-dicarboxylate;
dimethyl 2-(n-butyl)indole-3,6-dicarboxylate.
methyl 2-(n-butyl)indole-3-trifluoroacetyl-7-carboxylate;
methyl 2-(n-butyl)-7-methoxyindole-3-carboxylate;
methyl 2-(n-butyl)-6-fluoroindole-3-carboxylate;
dimethyl 2-(n-butyl)indole-3,5-dicarboxylate;
methyl 2-(n-butyl)-4-methylindole-3-carboxylate; and
methyl 2-(n-butyl)-6-chloro-7-methylindole-3-carboxylate.

PREPARATION 12

Preparation of Compounds of Formula (R)

A. Preparation of (R) where $R^2$ is n-Butyl, X is 3-Methoxycarbonyl, Y is 7-Methoxycarbonyl, and Z is Hydrogen Dimethyl 2-(n-butyl)indole-3,7-dicarboxylate (Q) (4.5 g) (prepared, e.g., as described in Preparation 11), in DMF (40 ml) was treated with sodium hydride (0.7 g of 60% mineral oil dispersion) at 0° C., and the resulting mixture was stirred for 30 minutes at 0° C. 2'-(Cyano)-biphenyl-4-ylmethyl bromide (4.4 g) was added and the mixture was allowed to come to room temperature. Water was added and the mixture was extracted with ethyl acetate. The ethyl acetate extract was washed with water, brine, then dried over sodium sulfate and evaporated under reduced pressure. Chromatography on silica gel, eluting with 25% ethyl acetate-hexane, afforded dimethyl 2-(n-butyl)-1-(2''-cyanobiphenyl-4'-ylmethyl)indole-3,7-dicarboxylate (1.7 g), a compound of Formula (R), as a white solid.

B. Preparation of (R) where $R^2$ is n-Butyl, Y is 6-Methoxycarbonyl, and X and Z are Hydrogen Similarly, following the procedures of Preparation 12A above, but replacing dimethyl 2-(n-butyl)indole-3,7-dicarboxylate with methyl 2-(n-butyl)indole-6-carboxylate, the following intermediate of Formula (R) was prepared:

methyl 2-(n-butyl)-1-(2''-cyanobiphenyl-4'-ylmethyl)indole-6-carboxylate.

C. Preparation of (R) where $R^2$ is n-Butyl, Y is 7-Methoxycarbonyl, X is Chloro, and Z is Hydrogen Similarly, following the procedures of Preparation 12A above, but replacing dimethyl 2-(n-butyl)indole-3,7-dicarboxylate with methyl 2-(n-butyl)-3-chloroindole-7-carboxylate and stirring the reaction mixture overnight at room temperature, the following intermediate of Formula (R) was prepared:

methyl 2-(n-butyl)-3-chloro-1-(2''-cyanobiphenyl-4'-ylmethyl)indole-7-carboxylate.

D. Preparation of (R), varying $R^2$, Y and Z

Similarly, following the procedures of Preparation 12A above, but replacing dimethyl 2-(n-butyl)indole-3,7-dicarboxylate with other compounds of Formula (P) or (Q), the following exemplary intermediates of Formula (R) are prepared:

dimethyl 2-ethyl-1-(2''-cyanobiphenyl-4'-ylmethyl)indole-3,7-dicarboxylate;

dimethyl 2-(n-propyl)-1-(2''-cyanobiphenyl-4'-ylmethyl)-indole-3,7-dicarboxylate;

dimethyl 2-(n-hexyl)-1-(2''-cyanobiphenyl-4'-ylmethyl)-indole-3,7-dicarboxylate;

dimethyl 2-(n-butyl)-1-(2''-cyanobiphenyl-4'-ylmethyl)indole-3,6-dicarboxylate;

2-(n-butyl)-7-methoxy-1-(2''-cyanobiphenyl-4'-ylmethyl)indole;

2-(n-butyl)-6-fluoro-1-(2''-cyanobiphenyl-4'-ylmethyl)indole;

methyl 2-(n-butyl)-1-(2''-cyanobiphenyl-4'-ylmethyl)-7-methoxyindole-3-carboxylate;

methyl 2-(n-butyl)-1-(2''-cyanobiphenyl-4'-ylmethyl)-6-fluoroindole-3-carboxylate;

dimethyl 2-(n-butyl)-1-(2''-cyanobiphenyl-4'-ylmethyl)-indole-3,5-dicarboxylate;

methyl 2-(n-butyl)-1-(2'''-cyanobiphenyl-4'-ylmethyl)-4-methylindole-3-carboxylate; and methyl 2-(n-butyl)-1-(2'''-cyanobiphenyl-4'-ylmethyl)-6-chloro-7-methylindole-3-carboxylate.

PREPARATION 13

Preparation of Compounds of Formula (S)

A. Preparation of (S) where $R^2$ is Ethyl, Y is 3-Methoxycarbonyl, and Z is Hydrogen A solution of methyl 2-nitro-3-(hexan-2-one)benzoate (O) (1.0 g), ethylene glycol (0.4 g), and p-toluenesulfonic acid (50 mg) in toluene (20 ml) was heated under reflux (120°–125° C.) for 12 hours. Water formed during the course of reaction was removed using a Dean-Stark separator. The reaction mixture was cooled and diluted with ethyl acetate (100 ml) and the resulting solution washed sequentially with sodium bicarbonate solution (5%), water and brine. The ethyl acetate layer was dried over magnesium sulfate and solvent was evaporated under reduced pressure. The residue was chromatographed on silica gel, eluting with 20% ethyl acetate-hexane, to give 1-(3-methoxycarbonyl-2-nitrophenyl)butan-2-one ethylene ketal (1.17 g), a compound of Formula (S), as an oil.

B. Preparation of (S) where Y is 3-methoxycarbonyl varying $R^2$ and Z

Similarly, following the procedures of Preparation 13A above, but replacing methyl 2-nitro-3-(hexan-2-one)benzoate with other compounds of Formula (O), the following exemplary intermediates of Formula (S) are prepared 1-(3-methoxycarbonyl-2-nitro-5-methylphenyl)butan-2-one ethylene ketal;

1-(3-methoxycarbonyl-2-nitrophenyl)pentan-2-one ethylene ketal;

1-(3-methoxycarbonyl-2-nitrophenyl)hexan-2-one ethylene ketal;

1-(3-methoxycarbonyl-2-nitrophenyl)octan-2-one ethylene ketal;

1-(3-methoxy-2-nitrophenyl)butan-2-one ethylene ketal;

1-(4-fluoro-2-nitrophenyl)butan-2-one ethylene ketal;

1-(5-carbomethoxy-2-nitrophenyl)butan-2-one ethylene ketal;

1-(6-methyl-2-nitrophenyl)butan-2-one ethylene ketal; and 1-(5-chloro-6-methyl-2-nitrophenyl)butan-2-one ethylene ketal.

PREPARATION 14

Preparation of Compounds of Formula (T)

A. Preparation of (T) where $R^2$ is Ethyl, Y is 3-Methoxycarbonyl, and Z is Hydrogen To a solution of 1-(3-methoxycarbonyl-2-nitrophenyl)butan-2-one ethylene ketal (S) (1.12 g) (prepared, e.g., as described in Preparation 13), in absolute ethanol (50 ml) was added palladium on carbon (150 mg, 10%), and the mixture stirred under hydrogen at atmospheric pressure and room temperature for 6 hours. The reaction mixture was passed through a Celite pad to remove catalyst, and the pad was washed with methylene chloride. The combined filtrate and washings were concentrated under reduced pressure to give 1-(2-amino-3-methoxycarbonylphenyl)butan-2-one ethylene ketal (0.98 g), a compound of Formula (T), as a colorless oil.

B. Preparation of (T) where Y is 3-methoxycarbonyl, varying R² and Z

Similarly, following the procedures of Preparation 14A above, but replacing 1-(3-methoxycarbonyl-2-nitrophenyl)butan-2-one ethylene ketal with other compounds of Formula (S), the following exemplary intermediates of Formula (T) are prepared:

1-(3-methoxycarbonyl-2-amino-5-methylphenyl)butan-2-one ethylene ketal;
1-(3-methoxycarbonyl-2-aminophenyl)pentan-2-one ethylene ketal;
1-(3-methoxycarbonyl-2-aminophenyl)hexan-2-one ethylene ketal;
1-(3-methoxycarbonyl-2-aminophenyl)octan-2-one ethylene ketal;
1-(3-methoxy-2-aminophenyl)butan-2-one ethylene ketal;
1-(4-fluoro-2-aminophenyl)butan-2-one ethylene ketal;
1-(5-carbomethoxy-2-aminophenyl)butan-2-one ethylene ketal;
1-(6-methyl-2-aminophenyl)butan-2-one ethylene ketal; and
1-(5-chloro-6-methyl-2-aminophenyl)butan-2-one ethylene ketal.

PREPARATION 15

Preparation of Compounds of Formula (U)

A. Preparation of (U) where R² is Ethyl, Y is 3-Methoxycarbonyl, and Z is Hydrogen A mixture of 1-(2-amino-3-methoxycarbonylphenyl)butan-2-one ethylene ketal (T) (0.7 g) (prepared, e.g., as described in Preparation 14), 2'-(cyano)biphenyl-4-ylmethylbromide (0.826 g) and potassium carbonate (0.41 g) in dimethylformamide (20 ml) was heated at 80°-90° C. for 16 hours under an inert atmosphere. The reaction mixture was concentrated under reduced pressure, and the residue obtained was diluted with ethyl acetate (100 ml), washed twice with cold water, and then brine. The solvent was removed under reduced pressure and the residue was chromatographed on silica gel, eluting with 20% ethyl acetate/hexane, to give 1-[2-(2''-cyanobiphenyl-4'-ylmethylamino)-3-methoxycarbonylphenyl]butan-2-one ethylene ketal (0.52 g), a compound of Formula (U), as an oil.

B. Preparation of (U) where Y is 3-methoxycarbonyl varying R² and Z

Similarly, following the procedures of Preparation 15A above, but replacing 1-(2-amino-3-methoxycarbonylphenyl)butan-2-one ethylene ketal with other compounds of Formula (T), the following exemplary intermediates of Formula (U) are prepared:

1-[2-(2''-cyanobiphenyl-4'-ylmethylamino)-3-methoxycarbonyl-5-methylphenyl]butan-2-one ethylene ketal;
1-[2-(2''-cyanobiphenyl-4'-ylmethylamino)-3-methoxycarbonylphenyl]pentan-2-one ethylene ketal;
1-[2-(2''-cyanobiphenyl-4'-ylmethylamino)-3-methoxycarbonylphenyl]hexan-2-one ethylene ketal;
1-[2-(2''-cyanobiphenyl-4'-ylmethylamino)-3-methoxycarbonylphenyl]octan-2-one ethylene ketal;
1-[2-(2''-cyanobiphenyl-4'-ylmethylamino)-3-methoxyphenyl)butan-2-one ethylene ketal;
1-[2-(2''-cyanobiphenyl-4'-ylmethylamino)-4-fluorophenyl)butan-2-one ethylene ketal;
1-[2-(2''-cyanobiphenyl-4'-ylmethylamino)-5-methoxycarbonylphenyl)butan-2-one ethylene ketal;
1-[2-(2''-cyanobiphenyl-4'-ylmethylamino)-6-methylphenyl)butan-2-one ethylene ketal; and
1-[2-(2''-cyanobiphenyl-4'-ylmethylamino)-5-chloro-6-methylphenyl)butan-2-one ethylene ketal.

PREPARATION 16

Preparation of Compounds of Formula (V)

A. Preparation of (V) where R² is Ethyl, Y is 7-Methoxycarbonyl, and Z is Hydrogen A solution of 1-[2-(2''-cyanobiphenyl-4'-ylmethylamino)-3-methoxycarbonylphenyl]butan-2-one ethylene ketal (U) (0.5 g) (prepared, e.g., as described in Preparation 15), in tetrahydrofuran (50 ml) containing hydrochloric acid (2N, 5 ml) was stirred at 40° C. for 2 hours. The reaction mixture was cooled and diluted with methylene chloride (100 ml), and the resulting solution was carefully neutralized with cold ammonium hydroxide solution. The organic layer was separated, and the aqueous layer was extracted twice with methylene chloride. The combined methylene chloride extracts were washed with water and brine and then dried over magnesium sulfate. The solvent was removed under reduced pressure and the residue was chromatographed on silica gel, eluting with 20% ethyl acetate/hexane, to give methyl 2-ethyl-1-(2''-cyanobiphenyl-4'-ylmethyl)indole-7-carboxylate (0.41 g), a compound of Formula (V), an oil.

B. Preparation of (V), varying R², Y and Z

Similarly, following the procedures of Preparation 16A above, but replacing 1-[2-(2''-cyanobiphenyl-4'-ylmethylamino)-3-methoxycarbonylphenyl]butan-2-one ethylene ketal with other compounds of Formula (U), the following exemplary intermediates of Formula (V) are prepared:

methyl 2-(n-propyl)-1-(2''-cyanobiphenyl-4'-ylmethyl)indole-7-carboxylate;
methyl 2-(n-butyl)-1-(2''-cyanobiphenyl-4'-ylmethyl)indole-7-carboxylate;
methyl 2-(n-hexyl)-1-(2''-cyanobiphenyl-4'-ylmethyl)indole-7-carboxylate;
2-(n-butyl)-7-methoxy-1-(2''-cyanobiphenyl-4'-ylmethyl)indole;
2-(n-butyl)-6-fluoro-1-(2''-cyanobiphenyl-4'-ylmethyl)indole;
methyl 2-(n-butyl)-1-(2''-cyanobiphenyl-4'-ylmethyl)indole-5-carboxylate;
2-(n-butyl)-4-methyl-1-(2''-cyanobiphenyl-4'-ylmethyl)indole; and
2-(n-butyl)-5-chloro-4-methyl-1-(2''-cyanobiphenyl-4'-ylmethyl)indole.

PREPARATION 17

Preparation of Compounds of Formula (X)

A. Preparation of (X) where Y and Z are Hydrogen

A solution of 2-amino-3-methylpyridine (10.8 g) and di-tert-butyl dicarbonate (21.8 g) in tetrahydrofuran was heated under reflux for 12 hours. Evaporation afforded a solid which was recrystallized from ether-tetrahydrofuran to yield 2-(t-butoxycarbonylamino)-3- methylpyridine (10.2 g), a compound of Formula (X), m.p. 132°–133° C.

B. Preparation of (X), varying Y and Z

Similarly, following the procedures of Preparation 17A above, but replacing 2-amino-3-methylpyridine with other compounds of Formula (W), the following exemplary intermediates of Formula (X) are prepared:
 2-(t-butoxycarbonylamino)-3-methyl-4-methoxypyridine;
 2-(t-butoxycarbonylamino)-3,5-dimethylpyridine;
 2-(t-butoxycarbonylamino)-3-methyl-5-fluoropyridine; and
 2-(t-butoxycarbonylamino)-3,4-dimethyl-6-chloropyridine.

PREPARATION 18

Preparation of Compounds of Formula (Y)

A. Preparation of (Y) where $R^2$ is n-Butyl and Y and Z are Hydrogen

A solution of 2-(t-butoxycarbonylamino)-3-methylpyridine (X) (5.3 g) (prepared, e.g., as described in Preparation 17), in tetrahydrofuran (100 ml) was cooled to −50° C. and a solution of sec-butyllithium (46 ml of 1.3M in cyclohexane) was added. After 10 minutes, the dark solution was treated with N-methoxy-N-methylvaleramide (4.4 g) and the resulting solution was stirred 10 minutes. The mixture was diluted with ether, washed with water, dried over sodium sulfate and evaporated. Crystallization of the residue from hexane afforded 1-[2-(t-butoxycarbonylamino)pyridin-3-yl]hexan-2-one (4.3 g), a compound of Formula (Y), as a white solid m.p. 66°–67° C.

B. Preparation of (Y), varying $R^2$, Y and Z

Similarly, following the procedures of Preparation 18A above, but replacing 2-(t-butoxycarbonylamino)-3-methylpyridine with other compounds of Formula (X), the following exemplary intermediates of Formula (Y) are prepared:
 1-[2-(t-butoxycarbonylamino)pyridin-3-yl]butan-2-one;
 1-[2-(t-butoxycarbonylamino)pyridin-3-yl]pentan-2-one;
 1-[2-(t-butoxycarbonylamino)pyridin-3-yl]octan-2-one;
 1-[2-(t-butoxycarbonylamino)pyridin-3-yl]hexan-2-one;
 1-[2-(t-butoxycarbonylamino)-4-methoxypyridin-3-yl]hexan-2-one;
 1-[2-(t-butoxycarbonylamino)-5-methylpyridin-3-yl]hexan-2-one;
 1-[2-(t-butoxycarbonylamino)-5-fluoropyridin-3-yl]hexan-2-one; and
 1-[2-(t-butoxycarbonylamino)-6-chloro-4-methylpyridin-3-yl]hexan-2-one.

PREPARATION 19

Preparation of Compounds of Formula (AB)

A. Preparation of (AB) where $R^2$ is n-Butyl and Y and Z are Hydrogen

A solution of 1-[2-(t-butoxycarbonylamino)pyridin-3-yl]hexan-2-one (Y) (4.2 g) (prepared, e.g, as described in Preparation 18), in dichloromethane (25 ml) and trifluoroacetic acid (10 ml) was stirred at room temperature overnight. The solution was concentrated under vacuum and the residue was partitioned between aqueous ammonium hydroxide and ether. The ether layer was washed with brine, dried, and the solvent was evaporated. The residue was further purified by silica gel chromatography, eluting with 30% ethyl acetate-hexane, to give 2-(n-butyl)-7-azaindole (2.9 g), a compound of Formula (AB), as an oil, which crystallized on standing to a solid, m.p. 46°–47° C.

B. Preparation of (AB), varying $R^2$, Y and Z

Similarly, following the procedures of Preparation 19A above, but replacing 1-[2-(t-butoxycarbonylamino)pyridin-3-yl]hexan-2-one with other compounds of Formula (Y), the following exemplary intermediates of Formula (AB) are prepared:
 2-ethyl-7-azaindole;
 2-(n-propyl)-7-azaindole;
 2-(n-hexyl)-7-azaindole;
 2-(n-butyl)-4-methoxy-7-azaindole;
 2-(n-butyl)-6-methyl-7-azaindole;
 2-(n-butyl)-4,6-dimethyl-7-azaindole;
 2-(n-butyl)-5-fluoro-7-azaindole; and
 2-(n-butyl)-6-chloro-4-methyl-7-azaindole.

PREPARATION 20

Preparation of Compounds of Formula (AC)

A. Preparation of (AC) where $R^2$ is n-Butyl and Y and Z are Hydrogen

A solution of 2-(n-butyl)-7-azaindole (AB) (0.87 g) (prepared, e.g., as described in Preparation 19), in DMF (30 ml) was treated with sodium hydride (0.26 g of 60% mineral oil dispersion) at 20° C. and the resulting mixture was stirred 20 minutes at room temperature, then cooled to 0° C. 2'-(Cyano)biphenyl-4-ylmethyl bromide (1.47 g, 6 mmol) was added and the mixture was allowed to come to room temperature. Water was added and the mixture was extracted with ethyl acetate. The ethyl acetate extract was washed with water and brine, dried over sodium sulfate and evaporated. Chromatography on silica gel, eluting with 25% ethyl acetate/hexane, afforded 2-(n-butyl)-1-(2''-cyanobiphenyl-4'-ylmethyl)-1H-pyrrolo[2,3-b]pyridine (1.13 g), a compound of Formula (AC), as a white solid, m.p. 86°–88° C.

B. Preparation of (AC), varying $R^2$, Y and Z

Similarly, following the procedures of Preparation 20A above, but replacing 2-(n-butyl)-7-azaindole with other compounds of Formula (AB), the following exemplary intermediates of Formula (AC) are prepared
 2-ethyl-1-(2''-cyanobiphenyl-4'-ylmethyl)-1H-pyrrolo[2,3-b]pyridine;
 2-(n-propyl)-1-(2''-cyanobiphenyl-4'-ylmethyl)-1H-pyrrolo[2,3-b]pyridine;
 2-(n-hexyl)-1-(2''-cyanobiphenyl-4'-ylmethyl)-1H-pyrrolo[2,3-b]pyridine;
 2-(n-butyl)-1-(2''-cyanobiphenyl-4'-ylmethyl)-4-methoxy-1H-pyrrolo[2,3-b]pyridine;
 2-(n-butyl)-1-(2''-cyanobiphenyl-4'-ylmethyl)-6-methyl-1H-pyrrolo[2,3-b]pyridine;
 2-(n-butyl)-1-(2''-cyanobiphenyl-4'-ylmethyl)-4,6-dimethyl-1H-pyrrolo[2,3-b]pyridine;
 2-(n-butyl)-1-(2''-cyanobiphenyl-4'-ylmethyl)-5-fluoro-1H-pyrrolo[2,3-b]pyridine; and
 2-(n-butyl)-1-(2''-cyanobiphenyl-4'-ylmethyl)-6-chloro-4-methyl-1H-pyrrolo[2,3-b]pyridine.

PREPARATION 21

A. Preparation of (AE) where $R^2$ is n-Butyl

To a cold (0° C.) suspension of NaH (5.4 g, 60% suspension in mineral oil) in anhydrous ether (180 ml) was added dropwise a mixture of 1-n-butyltosylmethylisocyanide (29 g) and methyl butadienecarboxylate (;2.2 ml) in anhydrous ether (180 ml) and dry dimethyl sulfoxide (90 ml) under an inert atmosphere. The reaction mixture was first stirred at 0° C. for 1 hour and then slowly brought to room temperature and the stirring continued for an additional 6 hours. The reaction mixture was then cooled to 0° C. and cautiously poured onto aqueous saturated ammonium chloride solution (200 ml). The organic layer was separated, and the aqueous layer was thoroughly extracted with ethyl acetate. The combined ether and ethyl acetate extracts were sequentially washed with saturated ammonium chloride solution in cold water, and then brine, and dried with magnesium sulfate. The solvent was removed under vacuum and the residue purified by column chromatography on silica gel, eluting with 15% ethyl acetate/hexane, to afford methyl 3-[2-(n-butyl)-pyrrol-4-yl]acrylate as a yellow oil (15.32 g), a compound of Formula (AE), which crystallized on standing to a solid, m.p. 65°–67° C.

B. Preparation of (AE), varying $R^2$

Similarly, following the procedures of Preparation 21A above, but replacing 1-n-butyltosylmethylisocyanide with other compounds of Formula (AD), the following exemplary intermediates of Formula (AE) are prepared:

methyl 3-(2-ethylpyrrol-4-yl)acrylate;
methyl 3-[2-(2-n-propyl)pyrrol-4-yl]acrylate; and
methyl 3-[2-(n-hexyl)pyrrol-4-yl]acrylate.

PREPARATION 22

Preparation of Compounds of Formula (AF)

A. Preparation of (AF) where $R^2$ is n-Butyl

Methyl 3-[2-(n-butyl)pyrrol-4-yl]acrylate (AE) (6.2 g) (prepared, e.g., as described in Preparation 21), in DMF (200 ml) was treated with sodium hydride (1.8 g of 60% mineral oil dispersion) at 0° C., and the resulting mixture was stirred for 30 minutes at 0° C. 2'-(Cyano)-biphenyl-4-ylmethyl bromide (9.8 g) was added, and the mixture allowed to come to room temperature. Water was added, and the mixture was extracted with ethyl acetate. The ethyl acetate extract was washed with water, brine, dried over sodium sulfate and evaporated. The residue was chromatographed on silica gel, eluting with 25% ethyl acetate/hexane, affording methyl 3-[2-(n-butyl)-1-(2''-cyanobiphenyl-4'-ylmethyl)pyrrol-4-yl]acrylate (9.17 g), a compound of Formula AF, as an oil.

B. Preparation of (AF), varying $R^2$

Similarly, following the procedures of Preparation 22A above, but replacing methyl 3-[2-(n-butyl)pyrrol-4-yl]acrylate with other compounds of Formula (AE), the following exemplary intermediates of Formula (AF) are prepared:

3-[2-ethyl-1-(2''-cyanobiphenyl-4'-ylmethyl)pyrrol-4-yl]acrylate;
3-[2-(n-propyl)-1-(2''-cyanobiphenyl-4'-ylmethyl)pyrrol-4-yl]acrylate; and
3-[2-(n-hexyl)-1-(2''-cyanobiphenyl-4'-ylmethyl)pyrrol-4-yl]acrylate.

PREPARATION 23

Preparation of Compounds of Formula (AG)

A. Preparation of (AG) where $R^2$ is n-Butyl

To a solution of methyl 3-[2-(n-butyl)-1-(2''-cyanobiphenyl-4'-ylmethyl)pyrrol-4-yl]acrylate (AF) (6.0 g) (prepared, e.g., as described in Preparation 22), in methylene chloride (200 ml) was added 5% palladium on carbon (1 g), and the resulting mixture was stirred under hydrogen at room temperature at atmospheric pressure for 4 hours. The reaction mixture was filtered through a Celite pad to remove catalyst, and evaporation of the filtrate gave methyl 3-[2-(n-butyl)-1-(2''-cyanobiphenyl-4'-ylmethyl)pyrrol-4-yl]propionate (6.0 g), a compound of Formula (AG), as an oil.

B. Preparation of (AG), varying $R^2$

Similarly, following the procedures of Preparation 23A above, but replacing methyl 3-[2-(n-butyl)-1-(2''-cyanobiphenyl-4'-ylmethyl)pyrrol-4-yl]acrylate with other compounds of Formula (AF), the following exemplary intermediates of Formula (AG) are prepared:

methyl 3-[2-ethyl-1-(2''-cyanobiphenyl-4'-ylmethyl)pyrrol-4-yl]propionate;
methyl 3-[2-(n-propyl)-1-(2''-cyanobiphenyl-4'-ylmethyl)pyrrol-4-yl]propionate; and
methyl 3-[2-(n-hexyl)-1-(2''-cyanobiphenyl-4'-ylmethyl)pyrrol-4-yl]propionate.

PREPARATION 24

Preparation of Compounds of Formula (AH)

A. Preparation of (AH) where $R^2$ is n-Butyl

To a solution of methyl 3-[2-(n-butyl)-1-(2''-cyanobiphenyl-4'-ylmethyl)pyrrol-4-yl]propionate (AG) (5.8 g) (prepared, e.g., as described in Preparation 23), in methanol (100 ml) was added 10% sodium hydroxide solution (35 ml), and the resulting solution was gently heated under reflux for 4 hours. After cooling to 0° C., the solution was acidified to pH 6 with hydrochloric acid solution (6N), and the product thoroughly extracted into methylene chloride. The combined methylene chloride extracts were washed with cold water, brine, and then dried with magnesium sulfate. Removal of the solvent under vacuum gave 3-[(2-(n-butyl)-1-(2''-cyanobiphenyl-4'-ylmethyl)pyrrol-4-yl]propionic acid (5.51 g), a compound of Formula (AH), as a slightly pinkish gum.

B. Preparation of (AH), varying $R^2$

Similarly, following the procedures of Preparation 24A above, but replacing methyl 3-[2-(n-butyl)-1-(2''-cyanobiphenyl-4'-ylmethyl)pyrrol-4-yl]propionate with other compounds of Formula (AG), the following exemplary intermediates of Formula (AH) are prepared:

3-[2-ethyl-1-(2''-cyanobiphenyl-4'-ylmethyl)pyrrol-4-yl]propionic acid;
3-[2-(n-propyl)-1-(2''-cyanobiphenyl-4'-ylmethyl)pyrrol-4-yl]propionic acid; and
3-[2-(n-hexyl)-1-(2''-cyanobiphenyl-4'-ylmethyl)pyrrol-4-yl]propionic acid.

PREPARATION 25

Preparation of Compounds of Formula (AI)

A. Preparation of (AI) where $R^2$ is n-Butyl

To a suspension of 3-[(2-(n-butyl)-1-(2″-cyanobiphenyl-4′-ylmethyl)pyrrol-4-yl]propionic acid (AH) (5.5 g) (prepared, e.g., as described in Preparation 24), in water (8 ml) was added acetone (40 ml), and the solution was cooled to 0° C. To this solution was slowly added triethylamine (2.6 ml) in acetone (20 ml), and the resulting reaction mixture was stirred for 20 minutes at 0° C. A solution of ethyl chloroformate (20 mmol) in acetone (20 ml) was then slowly added while stirring at 0° C. After stirring for an additional 1 hour at 0° C., a solution of sodium azide (1.48 g) in water was added dropwise, and stirring was continued for 1 hour at 0° C. The reaction mixture was then poured onto crushed ice, and the product thoroughly extracted into ethyl acetate. The combined extracts were washed with cold water, brine, then dried with magnesium sulfate The solvent was removed under reduced pressure, and the residue dissolved in toluene (50 ml). The toluene solution was heated for 1 hour on a steam bath, excluding moisture. Removal of the solvent under reduced pressure gave a crude isocyanate (5.42 g, 14.2 mmol).

The crude isocyanate obtained above was dissolved in anhydrous ether (200 ml) and boron trifluoride-diethyl ether complex (2.0 ml) was added and the resulting mixture was stirred at 10° C. for 2 hours under an inert atmosphere. The reaction mixture was treated with ice, then diluted with saturated ammonium chloride solution (50 ml). The ether layer was separated, and the aqueous layer was thoroughly extracted with methylene chloride. The combined organic extracts were washed with brine, dried with magnesium sulfate and evaporated under reduced pressure. The crude product was crystallized from ethyl acetate to give 2-(n-butyl)-1-(2″-cyanobiphenyl-4′-ylmethyl)-4,5,6,7-tetrahydro-1H-pyrrolo[2,3-c]pyridin-7-one (4.37 g), a compound of Formula (AI), m p. 98°-100° C.

B. Preparation of (AI), varying $R^2$

Similarly, following the procedures of Preparation 25A above, but replacing 3-[(2-(n-butyl)-1-(2″-cyanobiphenyl-4′-ylmethyl)pyrrol-4-yl]propionic acid with other compounds of Formula (AH), the following exemplary intermediates of Formula (AI) are prepared:

2-ethyl-1-(2″-cyanobiphenyl-4′-ylmethyl)-4,5,6,7-tetrahydro-1H-pyrrolo[2,3-c]pyridin-7-one; 2-(n-propyl)-1-(2″-cyanobiphenyl-4′-ylmethyl)-4,5,6,7-tetrahydro-1H-pyrrolo[2,3-c]pyridin-7-one; and 2-(n-hexyl)-1-(2″-cyanobiphenyl-4′-ylmethyl)-4,5,6,7-tetrahydro-1H-pyrrolo[2,3-c]pyridin-7-one.

PREPARATION 26

Preparation of Compounds of Formula (AJ)

A. Preparation of (AJ) where $R^2$ is n-Butyl and $R^3$ is Methyl

A solution of 2-(n-butyl)-1-(2″-cyanobiphenyl-4′-ylmethyl)-4,5,6,7-tetrahydro-1H-pyrrolo[2,3-c]pyridin-7-one (AI) (1.15 g) (prepared, e.g, as described in Preparation 25), in dry tetrahydrofuran (100 ml) was cooled to −70° C. under an argon atmosphere. To this stirring solution was added n-butyllithium (2.1 ml, 1.6M in hexane) and the resulting solution was stirred for 15 minutes at −70° C., and then methyl iodide (0.4 ml) was added. The solution was slowly warmed to room temperature, stirred overnight, and then quenched with ammonium chloride. The mixture was then concentrated under vacuum, diluted with methylene chloride, washed with cold water, brine, and then dried over magnesium sulfate. Solvent was removed under reduced pressure, and the residue purified by silica gel chromatography, eluting with ethyl acetate/hexane, to yield 2-(n-butyl)-6-methyl-1-(2″-cyanobiphenyl-4′-ylmethyl)-4,5,6,7-tetrahydro-1H-pyrrolo[2,3-c]pyridin-7-one (1.018 g), a compound of Formula (AI), as a gum.

B. Preparation of (AJ), varying $R^2$ and $R^3$

Similarly, following the procedures of Preparation 26A above, but replacing 2-(n-butyl)-1-(2″-cyanobiphenyl-4′-ylmethyl)-4,5,6,7-tetrahydro-1H-pyrrolo[2,3-c]pyridin-7-one with other compounds of Formula (AI), the following exemplary intermediates of Formula (AJ) are prepared:

2-ethyl-6-methyl-1-(2″-cyanobiphenyl-4′-ylmethyl)-4,5,6,7-tetrahydro-1H-pyrrolo[2,3-c]pyridin-7-one;

2-(n-propyl)-6-methyl-1-(2″-cyanobiphenyl-4′-ylmethyl)-4,5,6,7-tetrahydro-1H-pyrrolo[2,3-c]pyridin-7-one;

2-(n-hexyl)-6-methyl-1-(2″-cyanobiphenyl-4′-ylmethyl)-4,5,6,7-tetrahydro-1H-pyrrolo[2,3-c]pyridin-7-one;

2-(n-butyl)-6-ethyl-1-(2″-cyanobiphenyl-4′-ylmethyl)-4,5,6,7-tetrahydro-1H-pyrrolo[2,3-c]pyridin-7-one; and 2-(n-butyl)-6-(n-butyl)-1-(2″-cyanobiphenyl-4′-ylmethyl)-4,5,6,7-tetrahydro-1H-pyrrolo[2,3-c]pyridin-7-one.

EXAMPLE 1

Preparation of Compounds of Formula (Ia)

A. Preparation of (Ia) where $R^1$ is n-Butyl, X is 3-carboxylic acid, and Y and Z are Hydrogen A mixture of 1-(n-butyl)-2-(2″-cyanobiphenyl-4′-ylmethyl)indole-3-carboxylic acid (L) (0.35 g) (prepared e.g., as described in Preparation 7), xylene (20 ml), and tributyltin azide (2 ml) was heated under reflux for about 20 hours. The mixture was then cooled in an ice bath, HCl in ether was added, and the mixture was stirred for 15 minutes. The mixture was filtered and washed with ether to yield 1-(n-butyl)-2-[2″-(1H-tetrazol-5-yl)biphenyl-4′-ylmethyl]indole-3-carboxylic acid (0.34 g), a compound of Formula (Ia), m.p. 200°-203° C.

B. Preparation of (Ia) where $R^1$ is n-Butyl, Z is Hydrogen, varying X and Y Similarly, following the procedures of Example 1A above, but replacing 1-(n-butyl)-2-(2″-cyanobiphenyl-4′-ylmethyl)indole-3-carboxylic acid with other compounds of Formula (L), the following compounds of Formula (Ia) were prepared:

1-(n-butyl)-2-[2″-(1H-tetrazol-5-yl)biphenyl-4′-ylmethyl]-3-trifluoroacetylindole, m.p. 223°-225° C.;

1-(n-butyl)-5-methoxy-2-[2″-(1H-tetrazol-5-yl)biphenyl-4′-ylmethyl]-3-trifluoroacetylindole, m.p. 214°-218° C.;

1-(n-butyl)-5-methoxy-2-[2″-(1H-tetrazol-5-yl)biphenyl-4′-ylmethyl]-3-carboxylic acid, m.p. 227° C.; and 1-(isopentyl)-2-[2″-(1H-tetrazol-5-yl)biphenyl-4′-ylmethyl]-3-carboxylic acid, m.p. 210°-212° C.

C. Preparation of (Ia), varying $R^1$, X, Y and Z

Similarly, following the procedures of Example 1A above, but replacing 1-(n-butyl)-2-(2''-cyanobiphenyl-4'-ylmethyl)-indole-3-carboxylic acid with other compounds of Formula (K) or (L), the following exemplary compounds of Formula (Ia) are prepared:

1-ethyl-2-[2''-(1H-tetrazol-5-yl)biphenyl-4'-ylmethyl]indole;

1-(2-propyl)-2-[2'''-(1H-tetrazol-5-yl)biphenyl-4'-ylmethyl]indole;

1-(n-hexyl)-2-[2''-(1H-tetrazol-5-yl)biphenyl-4'-ylmethyl]indole;

1-(n-butyl)-2-[2''-(1H-tetrazol-5-yl)biphenyl-4'-ylmethyl]4-methoxyindole;

1-(n-butyl)-2-[2''-(1H-tetrazol-5-yl)biphenyl-4'-ylmethyl]5-methylindole;

1-(n-butyl)-2-[2''-(1H-tetrazol-5-yl)biphenyl-4'-ylmethyl]6-hydroxyindole;

1-(n-butyl)-2-[2''-(1H-tetrazol-5-yl)biphenyl-4'-ylmethyl]7-fluoroindole;

1-(n-butyl)-2-[2''-(1H-tetrazol-5-yl)biphenyl-4'-ylmethyl]3-trifluoroacetyl-7-fluoroindole;

1-(n-butyl)-2-[2''-(1H-tetrazol-5-yl)biphenyl-4'-ylmethyl]7-chloro-5-methylindole;

1-(n-butyl)-3-chloro-2-[2''-(1H-tetrazol-5-yl)biphenyl-4'-ylmethyl]indole;

1-(n-butyl)-3-methyl-2-[2''-(1H-tetrazol-5-yl)biphenyl-4'-ylmethyl]indole;

1-ethyl-2-[2''-(1H-tetrazol-5-yl)biphenyl-4'-ylmethyl]indole-3-carboxylic acid;

1-(2-propyl)-2-[2''-(1H-tetrazol-5-yl)biphenyl-4'-ylmethyl]indole-3-carboxylic acid;

1-(n-hexyl)-2-[2''-(1H-tetrazol-5-yl)biphenyl-4'-ylmethyl]indole-3-carboxylic acid;

1-(n-butyl)-2-[2''-(1H-tetrazol-5-yl)biphenyl-4'-ylmethyl]-4-methoxyindole-3-carboxylic acid;

1-(n-butyl)-2-[2''-(1H-tetrazol-5-yl)biphenyl-4'-ylmethyl]-5-methylindole-3-carboxylic acid;

1-(n-butyl)-2-[2''-(1H-tetrazol-5-yl)biphenyl-4'-ylmethyl]-6-hydroxyindole-3-carboxylic acid;

1-(n-butyl)-2-[2''-(1H-tetrazol-5-yl)biphenyl-4'-ylmethyl]-7-fluoroindole-3-carboxylic acid;

1-(n-butyl)-2-[2''-(1H-tetrazol-5-yl)biphenyl-4'-ylmethyl]-7-chloro-5-methylindole-3-carboxylic acid;

EXAMPLE 2

Preparation of Compounds of Formula (Ia) where X is —$CONR^5R^6$

A. Preparation of (Ia) where $R^1$ is n-Butyl, X is 3-(N-piperidinocarbonyl), and Y and Z are Hydrogen A solution of 1-(n-butyl)-2-[2'''-(1H-tetrazol-5-yl)biphenyl-4'-ylmethyl]indole-3-carboxylic acid (0.4 g) (prepared, e.g, as described in Example 1), and carbonyldiimidazole (0.2 g) in acetonitrile (10 ml) was heated under reflux for 1 hour Piperidine (0.14 ml) and triethylamine (0.2 ml) were added, and the mixture was heated under reflux overnight. The mixture was then poured onto cold dilute HCl and extracted twice with ethyl acetate. The extract was washed with sodium bicarbonate, dried over magnesium sulfate, and evaporated under reduced pressure to yield 1-(n-butyl)-3-(N-piperidinocarbonyl)-2-[2''-(1H-tetrazol-5-yl)biphenyl-4'-ylmethyl]indole (0.43 g), a compound of Formula (Ia), m.p. 127°–130° C.

B. Preparation of (Ia) where $R^1$ is n-Butyl, X is 3-(N-methylaminocarbonyl), and Y and Z are Hydrogen Similarly, following the procedures of Example 2A above, but replacing piperidine with methylamine, the following compound of Formula (Ia) was prepared:

1-(n-butyl)-3-(N-methylaminocarbonyl)-2-[2''-(1H-tetrazol-5-yl)biphenyl-4'-ylmethyl]indole, m.p. 166° C.

C. Preparation of (Ia), varying $R^1$, X, Y and Z

Similarly, following the procedures of Example 2A above, but optionally replacing 1-(n-butyl)-2-[2''-(1H-tetrazol-5-yl)biphenyl-4'-ylmethyl]indole-3-carboxylic acid with other compounds of Formula (Ia) where X is —$CO_2H$, and optionally replacing piperidine with alkylamines of the formula $R^5R^6NH$, the following exemplary compounds of Formula (Ia) are prepared:

n-propyl 1-methyl-2-[2''-(1H-tetrazol-5-yl)biphenyl-4'-ylmethyl]indole-3-carboxylate;

ethyl 1-(n-butyl)-2-[2''-(1H-tetrazol-5-yl)biphenyl-4'-ylmethyl]indole-3-carboxylate;

1-ethyl-3-(N-methylcarboxamido)-2-[2''-(1H-tetrazol-5-yl)biphenyl-4'-ylmethyl]indole-3-carboxylic acid;

methyl 1-(2-propyl)-2-[2''-(1H-tetrazol-5-yl)biphenyl-4'-ylmethyl]indole-3-carboxylate; and 1-(n-hexyl)-3-(N-hexylcarboxamido)-2-[2''-(1H-tetrazol-5-yl)biphenyl-4'-ylmethyl]indole-3-carboxylic acid.

EXAMPLE 3

Preparation of Compounds of Formula (Ib)

A. Preparation of (Ib) where $R^2$ is n-Butyl, X is 3-Methoxycarbonyl, Y is 7-Methoxycarbonyl, and Z is Hydrogen A solution of dimethyl 2-(n-butyl)-1-[2''-cyanobiphenyl-4'-ylmethyl]indole-3,7-dicarboxylate (1.7 g) (prepared, e.g., as described in Preparation 12), and tributyltin azide (2.4 g) in xylene (20 ml) was heated under reflux for 48 hours. The solution was cooled to room temperature and then treated with a solution of hydrochloric acid in ether. The resulting mixture was stirred for 30 minutes. Filtration afforded dimethyl 2-(n-butyl)-1-[2''-(1H-tetrazol-5-yl)biphenyl-4'-ylmethyl]indole-3,7-dicarboxylate (1.6 g), a compound of Formula (Ib), m.p. 188°–189° C.

B. Preparation of (Ib) where $R^2$ is n-Butyl, X is 3-Methoxycarbonyl, and Z is Hydrogen, varying Y Similarly, following the procedures of Example 3A above, but replacing dimethyl 2-(n-butyl)-1-[2''-cyanobiphenyl-4'-ylmethyl]indole-3,7-dicarboxylate with other compounds of Formula (R), the following compounds of Formula (Ib) were prepared:

methyl 2-(n-butyl)-3-chloro-1-[2''-(1H-tetrazol-5-yl)biphenyl-4'-ylmethyl]indole-7-carboxylate;

methyl 2-(n-butyl)-1-[2''-(1H-tetrazol-5-yl)biphenyl-4'-ylmethyl]indole-6-carboxylate;

2-(n-butyl)-7-methoxy-1-[2''-(1H-tetrazol-5-yl)biphenyl-4'-ylmethyl]indole; and 2-(n-butyl)-5-methoxy-1-[2''-(1H-tetrazol-5-yl)biphenyl-4'-ylmethyl]indole.

C. Preparation of (Ib). varying $R^2$, Y and Z

Similarly, following the procedures of Example 3A above, but replacing dimethyl 2-(n-butyl)-1-[2''- cyanobiphenyl-4'-ylmethyl]indole-3,7-dicarboxylate with other compounds of Formula (R), the following exemplary compounds of Formula (Ib) are prepared:

dimethyl 2-ethyl-1-[2''-(1H-tetrazol-5-yl)biphenyl-4'-ylmethyl]indole-3,7-dicarboxylate;

dimethyl 2-(n-propyl)-1-[2''-(1H-tetrazol-5-yl)biphenyl-4'-ylmethyl]indole-3,7-dicarboxylate;

dimethyl 2-(n-hexyl)-1-[2''-(1H-tetrazol-5-yl)biphenyl-4'-ylmethyl]indole-3,7-dicarboxylate;

dimethyl 2-(n-butyl)-1-[2''-(1H-tetrazol-5-yl)biphenyl-4'-ylmethyl]indole-3,6-dicarboxylate;

methyl 2-(n-butyl)-1-[2''-(1H-tetrazol-5-yl)biphenyl-4'-ylmethyl]-7-methoxyindole-3-carboxylate;

methyl 2-(n-butyl)-1-[2''-(1H-tetrazol-5-yl)biphenyl-4'-ylmethyl]-6-fluoroindole-3-carboxylate;.

dimethyl 2-(n-butyl)-1-[2''-(1H-tetrazol-5-yl)biphenyl-4'-ylmethyl]-indole-3,5-dicarboxylate;

methyl 2-(n-butyl)-1-[2''-(1H-tetrazol-5-yl)biphenyl-4'-ylmethyl]-4-methylindole-3-carboxylate; and methyl 2-(n-butyl)-1-[2''-(1H-tetrazol-5-yl)biphenyl-4'ylmethyl]-6-chloro-7-methylindole-3-carboxylate.

EXAMPLE 4

Preparation of Compounds of Formula (Ib)

A. Preparation of (Ib) where $R^2$ is n-Butyl, X is 3-Carboxyl, Y is 7-Carboxyl, and Z is Hydrogen A mixture of dimethyl 2-(n-butyl)-1-[2''-(1H-tetrazol-5-yl)biphenyl-4'-ylmethyl]indole-3,7-dicarboxylate (1.5 g) (prepared, e.g., as described in Example 3), in water (35 ml) and 15% sodium hydroxide (5.3 ml) was heated under reflux for 2 hours. The resulting solution was cooled, acidified with hydrochloric acid and filtered to afford 2-(n-butyl)-1-[2''-(1H-tetrazol-5-yl)biphenyl-4'-ylmethyl]-3,7-dicarboxylic acid (1.3 g), a compound of Formula (Ib), as a white solid, m.p. 185°–186° C.

B. Preparation of (Ib), varying $R^2$, Y and Z

Similarly, following the procedures of Example 4A above, but replacing dimethyl 2-(n-butyl)-1-[2''-(1H-tetrazol-5-yl)biphenyl-4'-ylmethyl]indole-3,7-dicarboxylate with other compounds of Formula (Ib) where X or Y is $-CO_2R^4$, where $R^4$ is lower alkyl, the following compounds of Formula (Ib) were prepared:

2-(n-butyl)-3-chloro-1-[2''-(1H-tetrazol-5-yl)biphenyl-4'-ylmethyl]indole-7-carboxylic acid; and 2-(n-butyl)-1-[2''-(1H-tetrazol-5-yl)biphenyl-4'-ylmethyl]-6-carboxylic acid.

C. Preparation of (Ib), varying $R^2$, Y and Z

Similarly, following the procedures of Example 4A above, but replacing dimethyl 2-(n-butyl)-1-[2''-(1H-tetrazol- 5-yl)biphenyl-4'-ylmethyl]indole-3,7-dicarboxylate with other compounds of Formula (Ib) where X is $-CO_2R^4$, where $R^4$ is lower alkyl, the following exemplary compounds of Formula (Ib) are prepared:

2-ethyl-1-[2''-(1H-tetrazol-5-yl)biphenyl-4'-ylmethyl]-indole-3,7-dicarboxylic acid;

2-(n-propyl)-1-[2''-(1H-tetrazol-5-yl)biphenyl-4'-ylmethyl]indole-3,7-dicarboxylic acid;

2-(n-hexyl)-1-[2''-(1H-tetrazol-5-yl)biphenyl-4'-ylmethyl]indole-3,7-dicarboxylic acid;

2-(n-butyl)-1-[2''-(1H-tetrazol-5-yl)biphenyl-4'-ylmethyl]-3,6-dicarboxylic acid.

2-(n-butyl)-1-[2''-(1H-tetrazol-5-yl)biphenyl-4'-ylmethyl]-7-methoxyindole-3-carboxylic acid;

2-(n-butyl)-1-[2''-(1H-tetrazol-5-yl)biphenyl-4'-ylmethyl]-6-fluoroindole-3-carboxylic acid;

2-(n-butyl)-1-[2''-(1H-tetrazol-5-yl)biphenyl-4'-ylmethyl]-indole-3,5-dicarboxylic acid;

2-(n-butyl)-1-[2''-(1H-tetrazol-5-yl)biphenyl-4'-ylmethyl]-4-methylindole-3-carboxylic acid; and 2-(n-butyl)-1-[2''-(1H-tetrazol-5-yl)biphenyl-4'-ylmethyl]-6-chloro-7-methylindole-3-carboxylic acid.

EXAMPLE 5

Preparation of Compounds of Formula (Ib)

A. Preparation of (Ib) where $R^2$ is n-Butyl, X and Z are Hydrogen, and Y is 7-Carboxyl 2-(n-Butyl)-1-[2''-(1H-tetrazol-5-yl)biphenyl-4'-ylmethyl]indole-3,7-dicarboxylic acid ((Ib) where X is $-CO_2H$) (50 mg) (prepared, e.g., as described in Example 4), was heated in a 200° C. oil bath for several minutes. The melt was cooled and crystallized from ether-hexane to afford 2-(n-butyl)-1-[2''-(1H-tetrazol-5-yl)biphenyl-4'-ylmethyl]indole-7-carboxylic acid (28 mg), a compound of Formula ((Ib) where X is hydrogen), m.p. 205°–206° C.

B. Preparation of (Ib), varying $R^2$, Y and Z

Similarly, following the procedures of Example 5A above, but replacing 2-(n-butyl)-1-[2''-(1H-tetrazol-5-yl)biphenyl-4'-ylmethyl]indole-3,7-dicarboxylic acid with other compounds of Formula (Ib) where X is $-CO_2H$, the following exemplary compounds of Formula (Ib) are prepared:

2-ethyl-1-[2''-(1H-tetrazol-5-yl)biphenyl-4'-ylmethyl]-indole-7-carboxylic acid;

2-(n-propyl)-1-[2''-(1H-tetrazol-5-yl)biphenyl-4'-ylmethyl]indole-7-carboxylic acid;

2-(n-hexyl)-1-[2''-(1H-tetrazol-5-yl)biphenyl-4'-ylmethyl]indole-7-carboxylic acid;

2-(n-butyl)-1-[2''-(1H-tetrazol-5-yl)biphenyl-4'-ylmethyl]indole-6-carboxylic acid.

2-(n-butyl)-1-[2''-(1H-tetrazol-5-yl)biphenyl-4'-ylmethyl]-7-methoxyindole;

2-(n-butyl)-1-[2''-(1H-tetrazol-5-yl)biphenyl-4'-ylmethyl]-6-fluoroindole;

2-(n-butyl)-1-[2''-(1H-tetrazol-5-yl)biphenyl-4'-ylmethyl]-indole-5-carboxylic acid;

2-(n-butyl)-1-[2''-(1H-tetrazol-5-yl)biphenyl-4'-ylmethyl]-4-methylindole; and 2-(n-butyl)-1-[2''-(1H-tetrazol-5-yl)biphenyl-4'-ylmethyl]-6-chloro-7-methylindole.

EXAMPLE 6

Preparation of Compounds of Formula (Ib)

A. Preparation of (Ib) where $R^2$ is Ethyl, X and Z are Hydrogen, and Y is 7-Methoxycarbonyl A solution of methyl 2-ethyl-1-[(2''-cyano)biphenyl-4'-yl)methyl]indole-7-carboxylate (0.25 g) (V) (prepared, e.g., as described in Preparation 16), and tributyltin azide (1 ml) in xylene (15 ml) was heated under reflux (140°–150° C.) for 48 hours under an inert atmosphere The reaction mixture was cooled and poured into saturated potassium fluoride (20 ml), and tetrafluoroboric acid/diethylether complex (8 drops). The resulting mixture was stirred for 18 hours at room temperature and then concentrated under vacuum. The residue was diluted with water (50 ml), the pH of the solution was adjusted to 6 with glacial acetic acid, and the product was thoroughly extracted into methylene chloride. The combined methylene chloride extracts were washed with brine, then dried over magnesium sulfate and concentrated under vacuum. The residue obtained was chromatographed on silica gel, eluting with 5% methane/methylene chloride, to give methyl 2-ethyl-1-[2''-(1H-tetrazol-5-yl)biphenyl-4'-ylmethyl]indole-7-carboxylate (0.165 g), a compound of Formula (Ib), as a white solid m.p. 180°-182° C.

B. Preparation of (Ib). varying $R^2$, Y and Z

Similarly, following the procedures of Example 6A above, but replacing methyl 2-ethyl-1-[(2''-cyano)biphenyl-4'-yl)methyl]indole-7-carboxylate with other compounds of Formula (V), the following exemplary compounds of Formula (Ib) are prepared:

methyl 2-(n-propyl)-1-[2''-(1H-tetrazol-5-yl)biphenyl-4'-ylmethyl]indole-7-carboxylate;
methyl 2-(n-butyl)-1-[2''-(1H-tetrazol-5-yl)biphenyl-4'-ylmethyl]indole-7-carboxylate;
methyl 2-(n-hexyl)-1-[2''-(1H-tetrazol-5-yl)biphenyl-4'ylmethyl]indole-7-carboxylate;
2-(n-butyl)-7-methoxy-1-[2'''-(1H-tetrazol-5-yl)biphenyl-4'-ylmethyl]indole;
2-(n-butyl)-3-chloro-1-[2''-(1H-tetrazol-5-yl)biphenyl-4'-ylmethyl]indole;
2-(n-butyl)-3-methyl-1-[2''-(1H-tetrazol-5-yl)biphenyl-4'-ylmethyl]indole;
2-(n-butyl)-6-fluoro-1-[2''-(1H-tetrazol-5-yl)biphenyl-4'-ylmethyl]indole;
methyl 2-(n-butyl)-1-[2''-(1H-tetrazol-5-yl)biphenyl-4'-ylmethyl]indole-5-carboxylate;
2-(n-butyl)-4-methyl-1-[2''-(1H-tetrazol-5-yl)biphenyl-4'-ylmethyl]indole; and
2-(n-butyl)-5-chloro-4-methyl-1-[2'''-(1H-tetrazol-5-yl)biphenyl-4'-ylmethyl]indole.

EXAMPLE 7

Preparation of Compounds of Formula (Ib)

A. Preparation of (Ib) where $R^2$ is Ethyl, X and Z are Hydrogen, and Y is 7-Carboxyl A solution of methyl 2-ethyl-1-[2''-(1H-tetrazol-5-yl)biphenyl-4'-ylmethyl]indole-7-carboxylate (Ib) (0.12 g) (prepared, e.g., as described in Example 6), in sodium hydroxide solution (15%, 0.5 ml), methanol (2 m)), and water (5 ml) was heated at 100° C. for 3 hours. The reaction mixture was cooled and diluted with methylene chloride containing methanol (5%) and the resulting solution was acidified with hydrochloric acid (1N). The organic layer was separated and the aqueous layer was extracted twice with methylene chloride. The combined methylene chloride extracts were washed with cold water and brine and then dried over magnesium sulfate. The solvent was removed under reduced pressure, and the crude product was crystallized from methanol to give 2-ethyl-1-[2''-(1H-tetrazol-5-yl)biphenyl-4'-ylmethyl]indole-7-carboxylic acid (0.109 g), a compound of Formula (Ib), as a white solid m.p. 240°-243° C.

B. Preparation of (Ib), varying $R^2$, Y and Z

Similarly, following the procedures of Example 7A above, but replacing methyl 2-ethyl-1-[2''-(1H-tetrazol-5-yl)biphenyl-4'-yl)methyl]indole-7-carboxylate with other compounds of Formula (Ib) where Y is —$CO_2R^4$, where $R^4$ is lower alkyl, the following exemplary compounds of Formula (Ib) are prepared:

2-methyl-1-[2''-(1H-tetrazol-5-yl)biphenyl-4'-ylmethyl]indole-7-carboxylic acid;
2-(n-propyl)-1-[2''-(1H-tetrazol-5-yl)biphenyl-4'-ylmethyl]indole-7-carboxylic acid;
2-(n-butyl)-1-[2''-(1H-tetrazol-5-yl)biphenyl-4'-ylmethyl]indole-7-carboxylic acid;
2-(n-hexyl)-1-[2''-(1H-tetrazol-5-yl)biphenyl-4'-ylmethyl]indole-7-carboxylic acid; and
2-(n-butyl)-1-[2''-(1H-tetrazol-5-yl)biphenyl-4'-ylmethyl]indole-5-carboxylic acid.

EXAMPLE 8

Preparation of Compounds of Formula (II)

A. Preparation of (II) where $R^2$ is n-Butyl and X, Y and Z are Hydrogen

A solution of 2-(n-butyl)-1-(2''-cyanobiphenyl-4'-ylmethyl)-1H-pyrrolo[2,3-b]pyridine (AC) (0.25 g) (prepared, e.g., as described in Preparation 20), and tributyltin azide (1 ml) in xylene (10 ml) was heated under reflux for 48 hours under an inert atmosphere. The cooled solution was diluted with diethyl ether (100 ml), and aqueous saturated potassium fluoride solution (25 ml) and tetrafluoroboric acid/diethyl ether complex (0.5 ml) was added. The resulting mixture was stirred for 12 hours at room temperature and then concentrated under vacuum. The residue was diluted with water (50 ml), the pH of the solution was adjusted to 6 with acetic acid, and the product was thoroughly extracted in methylene chloride. The combined methylene chloride extracts were washed with brine, dried over magnesium sulfate, and concentrated under vacuum. The residue obtained was chromatographed on silica gel, eluting with 25% methanol-methylene chloride, to yield 2-(n-butyl)-1-[2''-(1H-tetrazol-5-yl)biphenyl-4'ylmethyl]-1H-pyrrolo[ 2,3-b ]pyridine (0.2 g), a compound of Formula (II), as a white solid, m.p. 86°-90° C.

B. Preparation of (II) where X is Hydrogen, varying $R^2$, Y and Z

Similarly, following the procedures of Example 8A above, but replacing 2-(n-butyl)-1-(2''-cyanobiphenyl-4'-ylmethyl)-1H-pyrrolo[2,3-b]pyridine with other compounds of Formula (AC), the following exemplary compounds of Formula (II) are prepared:

2-ethyl-1-[2''-(1H-tetrazol-5-yl)biphenyl-4'ylmethyl]-1H-pyrrolo[2,3-b]pyridine;
2-(n-propyl)-1-[2''-(1H-tetrazol-5-yl)biphenyl-4'ylmethyl]-1H-pyrrolo[2,3-b]pyridine;
2-(n-hexyl)-1-[2''-(1H-tetrazol-5-yl)biphenyl-4'ylmethyl]-1H-pyrrolo[2,3-b]pyridine;
2-(n-butyl)-1-[2''-(1H-tetrazol-5-yl)biphenyl-4'ylmethyl]-4-methoxy-1H-pyrrolo[2,3-b]pyridine;
2-(n-butyl)-3-chloro-1-[2''-(1H-tetrazol-5-yl)biphenyl-4'ylmethyl]-1H-pyrrolo[2,3-b]pyridine;
2-(n-butyl)-3-methyl-1-[2''-(1H-tetrazol-5-yl)biphenyl-4'ylmethyl]-1H-pyrrolo[2,3-b]pyridine;
2-(n-butyl)-1-[2''-(1H-tetrazol-5-yl)biphenyl-4'ylmethyl]-5-methyl-1H-pyrrolo[2,3-b]pyridine;
2-(n-butyl)-1-[2''-(1H-tetrazol-5-yl)biphenyl-4'ylmethyl]-5-fluoro-1H-pyrrolo[2,3-b]pyridine; and
2-(n-butyl)-1-[2''-(1H-tetrazol-5-yl)biphenyl-4'ylmethyl]-6-chloro-4-methyl-1H-pyrrolo[2,3-b]pyridine.

EXAMPLE 9

Preparation of Compounds of Formula (II) where X is —$CO_2R^4$

A. Preparation of (II) where $R^2$ is n-Butyl, X is 3-methoxycarbonyl, and Y and Z are Hydrogen A molar excess of a solution of phosgene in toluene is added to a solution of 2-(n-butyl)-1-[2'''-(1H-tetrazol-5-yl)biphenyl-4'-ylmethyl]-1H-pyrrolo[2,3-b]pyridine (a compound of Formula (II) where X is hydrogen, prepared, e.g., as described in Example 8), at 5° C. in dichloromethane (75 ml). The solution is stirred at room temperature for 16 hours, cooled in an ice bath, and treated with methanol (20 ml). Water is added and the dichloromethane layer is separated and evaporated under vacuum. Chromatography on silica gel, eluting with 20% ethyl acetate-hexane affords 2-(n-butyl)-3-methoxycarbonyl-1-[2'''-(1H-tetrazol-5-yl)biphenyl-4'-ylmethyl]-1H-pyrrolo[2,3-b]pyridine, a compound of Formula (II) where X is —$CO_2R^4$, as an oil.

B. Preparation of (II), varying $R^2$, Y and Z

Similarly, following the procedures of Example 9A above, but replacing 2-(n-butyl)-1-[2'''-(1H-tetrazol-5-yl)biphenyl-4'-ylmethyl]-1H-pyrrolo[2,3-b]pyridine with other compounds of Formula (II) where X is hydrogen, the following exemplary compounds of Formula (II) where X is —$CO_2R^4$ are prepared:

2-ethyl-3-methoxycarbonyl-1-[2'''-(1H-tetrazol-5-yl)biphenyl-4'-ylmethyl]-1H-pyrrolo[2,3-b]pyridine;

2-(n-propyl)-3-methoxycarbonyl-1-[2'''-(1H-tetrazol-5-yl)biphenyl-4'-ylmethyl]-1H-pyrrolo[2,3-b]pyridine;

2-(n-hexyl)-3-methoxycarbonyl-1-[2'''-(1H-tetrazol-5-yl)biphenyl-4'-ylmethyl]-1H-pyrrolo[2,3-b]pyridine;

2-(n-butyl)-3-methoxycarbonyl-1-[2'''-(1H-tetrazol-5-yl)biphenyl-4'ylmethyl]-4-methoxy-1H-pyrrolo[2,3-b]pyridine;

2-(n-butyl)-3-methoxycarbonyl-1-[2'''-(1H-tetrazol-5-yl)biphenyl-4'ylmethyl]-5-methyl-1H-pyrrolo[2,3-b]pyridine;

2-(n-butyl)-3-methoxycarbonyl-1-[2'''-(1H-tetrazol-5-yl)biphenyl-4'ylmethyl]-5-fluoro-1H-pyrrolo[2,3-b]pyridine; and 2-(n-butyl)-3-methoxycarbonyl-1-[2'''-(1H-tetrazol-5-yl)biphenyl-4'ylmethyl]-6-chloro-4-methyl-1H-pyrrolo[2,3-b]pyridine.

C. Preparation of (II), varying $R^2$, Y and Z

Similarly, following the procedures of Example 9A above, but optionally replacing 2-(n-butyl)-1-[2'''-(1H-tetrazol- 5-yl)biphenyl-4'-ylmethyl]-1H-pyrrolo[2,3-b]pyridine with other compounds of Formula (II) where X is hydrogen, and replacing phosgene with trifluoroacetic anhydride, the following exemplary compounds of Formula (II) where X is —$COCF_3$ are prepared:

2-ethyl-3-trifluoroacetyl-1-[2'''-(1H-tetrazol-5-yl)biphenyl-4'-ylmethyl]-1H-pyrrolo[2,3-b]pyridine;

2-(n-propyl)-3-trifluoroacetyl-1-[2'''-(1H-tetrazol-5-yl)biphenyl-4'-ylmethyl]-1H-pyrrolo[2,3-b]pyridine;

2-(n-hexyl)-3-trifluoroacetyl-1-[2'''-(1H-tetrazol-5-yl)biphenyl-4'-ylmethyl]-1H-pyrrolo[2,3-b]pyridine;

2-(n-butyl)-3-trifluoroacetyl-1-[2'''-(1H-tetrazol-5-yl)biphenyl-4'ylmethyl]-4-methoxy-1H-pyrrolo[2,3-b]pyridine;

2-(n-butyl)-3-trifluoroacetyl-1-[2'''-(1H-tetrazol-5-yl)biphenyl-4'ylmethyl]-5-methyl-1H-pyrrolo[2,3-b]pyridine;

2-(n-butyl)-3-trifluoroacetyl-1-[2'''-(1H-tetrazol-5-yl)biphenyl-4'ylmethyl]-5-fluoro-1H-pyrrolo[2,3-b]pyridine; and 2-(n-butyl)-3-trifluoroacetyl-1-[2'''-(1H-tetrazol-5-yl)biphenyl-4'ylmethyl]-6-chloro-4-methyl-1H-pyrrolo[2,3b]pyridine.

EXAMPLE 10

Preparation of Compounds of Formula (III)

A. Preparation of (III) where $R^2$ is n-Butyl and $R^3$ and X are Hydrogen

A solution of 2-(n-butyl)-1-(2''-cyanobiphenyl-4'-ylmethyl)-4,5,6,7-tetrahydro-1H-pyrrolo[2,3-c]pyridin-7-one (AI) (300 mg) (prepared, e.g., as described in Preparation 25), and tributyltin azide (1 ml) in xylene (10 ml) was heated under reflux for 48 hours under an inert atmosphere. The cooled solution was diluted with diethyl ether (100 ml), and aqueous saturated potassium fluoride solution (25 ml) and tetrafluoroboric acid/-diethyl ether complex (0.5 ml) was added. The resulting mixture was stirred for 12 hours at room temperature and then concentrated under vacuum. The residue was diluted with water (50 ml), the pH of the solution was adjusted to 6 with acetic acid, and the product was thoroughly extracted into methylene chloride. The combined methylene chloride extracts were washed with brine, then dried over magnesium sulfate and concentrated under reduced pressure. The residue obtained was chromatographed on silica gel, eluting with 25% methanol/methylene chloride, to yield 2-(n-butyl)-1-[2''-(1H-tetrazol-5-yl)biphenyl-4'-ylmethyl]-4,5,6,7-tetrahydro-1H-pyrrolo[2,3-c]pyridin-7-one (220 mg), a compound of Formula (III), as a white solid, m.p. 181°–183° C.

B. Preparation of (III) where $R^2$ is n-Butyl, $R^3$ is Methyl, and X is Hydrogen Similarly, following the procedures of Example 10A above, but replacing 2-(n-butyl)-1-(2''-cyanobiphenyl-4'-ylmethyl)-4,5,6,7-tetrahydro-1H-pyrrolo[2,3-c]pyridin-7-one with 2-(n-butyl)-6-methyl-1-(2''-cyanobiphenyl-4'-ylmethyl)-4,5,6,7-tetrahydro-1H-pyrrolo[2,3-c]pyridin-7-one (AJ), the following compound of Formula (III) was prepared:

2-(n-butyl)-6-methyl-1-[2''-(1H-tetrazol-5-yl)biphenyl-4'-ylmethyl]-4,5,6,7-tetrahydro-1H-pyrrolo[2,3-c]pyridin-7-one, m.p. 90°–95° C.

C. Preparation of (III), varying $R^2$, $R^3$ and X

Similarly, following the procedures of Example 10A above, but optionally replacing 2-(n-butyl)-1-(2''-cyanobiphenyl-4'-ylmethyl)-4,5,6,7-tetrahydro-1H-pyrrolo[2,3-c]pyridin-7-one with other compounds of Formula (AI) or (AJ), and optionally replacing methyl iodide with other lower alkyl halides, the following compounds of Formula (III) are prepared:

2-methyl-6-methyl-1-[2''-(1H-tetrazol-5-yl)biphenyl-4'-ylmethyl]-4,5,6,7-tetrahydro-1H-pyrrolo[2,3-c]pyridin-7-one;

2-ethyl-6-methyl-1-[2''-(1H-tetrazol-5-yl)biphenyl-4'-ylmethyl]-4,5,6,7-tetrahydro-1H-pyrrolo[2,3-c]pyridin-7-one;

2-(n-propyl)-6-methyl-1-[2'''-(1H-tetrazol-5-yl)biphenyl-4'-ylmethyl]-4,5,6,7-tetrahydro-1H-pyrrolo[2,3-c]pyridin-7-one;

2-(n-hexyl)-6-methyl-1-[2'''-(1H-tetrazol-5-yl)biphenyl-4'-ylmethyl]-4,5,6,7-tetrahydro-1H-pyrrolo[2,3-c]pyridin-7-one; 2-(n-butyl)-6-ethyl-1-[2'''-(1H-tetrazol-5-yl)biphenyl-4'-ylmethyl]-4,5,6,7-tetrahydro-1H-pyrrolo[2,3-c]pyridin-7-one; and 2-(n-butyl)-6-(n-butyl)-1-[2'''-(1H-tetrazol-5-yl)biphenyl-4'-ylmethyl]-4,5,6,7-tetrahydro-1H-pyrrolo[2,3-c]pyridin-7-one.

EXAMPLE 11

Preparation of Salts of Compounds of Formula (I), (II) and (III)

A. Conversion of 1-(n-butyl)-6-methoxy-2-[2''-(1H-tetrazol-5-yl)biphenyl-4'-ylmethyl]-indole to its Potassium Salt 1-(n-Butyl)-6-methoxy-2-[2''-(1H-tetrazol-5-yl)biphenyl-4'-ylmethyl]-indole (100 mg), prepared, e.g., as described in Example 1, was dissolved in methanol (20 ml), and a solution of potassium hydroxide (4.65 ml, 0.1M) in methanol was added. The solvent was evaporated to afford an oil, which was triturated with ethyl acetate to yield a white solid, potassium 1-(n-butyl)-6-methoxy-2-[2''-(1H-tetrazol-5-yl)biphenyl-4'-ylmethyl]-indole as a foam.

B. In a similar manner, all compounds of Formula (I), (II) or (III) form may be converted to the base addition salts by treatment with an appropriate base, for example, sodium bicarbonate, potassium carbonate, lithium hydroxide, ammonium hydroxide, calcium hydroxide, magnesium hydroxide, and the like. Base addition salts derived from organic bases include those formed from primary, secondary and tertiary amines, such as isopropylamine, diethylamine, trimethylamine, pyridine, cyclohexylamine, ethylene diamine, monoethanolamine, diethanolamine, triethanolamine, and the like.

In Examples 12 through 16 the active ingredient is 1-(n-butyl)-2-[2'''-(1H-tetrazol-5-yl)biphenyl-4'-ylmethyl]-indole-3-carboxylic acid. Other compounds of Formula (I), (II) or (III), and the pharmaceutically acceptable salts thereof, may be substituted therein.

EXAMPLE 12

| Composition for Oral Administration | |
|---|---|
| The composition contains: | % wt./wt. |
| Active ingredient | 40% |
| Lactose | 59.5% |
| Magnesium stearate | 0.5% |

The two ingredients are milled, mixed and dispensed into capsules containing 125-250 mg each; one capsule would approximate a total daily dosage of 50-100 mg.

EXAMPLE 13

| Composition for Oral Administration | |
|---|---|
| The composition contains: | % wt./wt. |
| Active ingredient | 50.0% |
| Microcrystalline cellulose | 45.0% |
| Croscarmellose sodium | 2.0% |
| PVP (polyvinylpyrrolidine) | 2.0% |
| Magnesium stearate | 1.0% |

The first four ingredients above are combined and granulated using water as solvent. The formulation is then dried, blended the magnesium stearate, and formed into tablets (containing 50-100 mg of active compound) with an appropriate tableting machine.

The compounds of the present invention may also be formulated in a solution for oral administration as follows:

| Active Ingredient | 10 mg/ml |
|---|---|
| Sucrose | 10 mg/ml |
| Sorbitol | 100 mg/ml |
| Sodium benzoate | 10 mg/ml |

HCL or NaOH to adjust pH to 3-7; q.s. to 1 ml with $H_2O$.

EXAMPLE 14

| Parenteral Formulation (IV) | |
|---|---|
| The composition contains: | % wt./wt. |
| Active ingredient | 2.00% |
| Propylene glycol | 20.0% |
| Polyethylene glycol 400 | 20.0% |
| Polysorbate 80 | 1.0% |
| 0.9% Saline solution qs ad | 100 ml |

The active ingredient is dissolved in propylene glycol, polyethylene glycol 400 and polysorbate 80. A sufficient quantity of 0.9% saline solution is then added with stirring to provide 100 ml. of the I.V. solution which is filtered through a 0.2 micron membrane filter and packaged under sterile conditions.

EXAMPLE 15

| Suppository Formulation | |
|---|---|
| The composition contains: | % wt./wt. |
| Active ingredient | 5.0% |
| Witepsol W | 95.0% |

The ingredients are melted together and mixed on a steam bath, and poured into molds containing 1-2 g total weight.

EXAMPLE 16

| Topical Fomulation | |
|---|---|
| Ingredients | grams |
| Active compound | 5-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 17

Determination of Affinity for Antiotensin II Receptors

Membranes of rat liver cells were homogenized (using a Polytron P10 tissue disrupter, setting 10 for 5 or 10 sec bursts) in 10 volumes (w/v) Tris buffer (pH 7.4 at 4° C.) of the following composition: Tris HCl (50 mM) and $Na_2$ EDTA (5 mM). The homogenate was centrifuged at $500 \times g$ and the supernatant retained. This procedure was repeated. The supernatant was rehomogenized and centrifuged at 30,000 to $48,000 \times g$, and the pellet resuspended in homogenizing buffer. Non-specific binding was determined using human angiotensin II (1.0 μM). AT-1 and AT-2 binding sites were labelled with [$^{125}$I]-Sar$^1$ Ile$^8$ AII (0.01 nM; New England Nuclear). Incubations of test compound, radiolabel, and AT-1 or AT-2 binding sites were terminated by vacuum filtration over Whatman GF/B glass fiber filters. After filtration, the filters were washed, dried and counted for radioactivity by liquid scintillation spectrometry with quench correction.

The concentration of test compound producing 50% inhibition of specific radioligand binding was determined by iterative curve fitting and its inhibition dissociation constant ($K_i$) calculated.

The compounds of the present invention were active in this assay.

EXAMPLE 18

Angiotensin Receptor Antagonism Functional Assays (a) Isolated ring segments of rabbit aorta were set up in Krebs'physiological salt solution at 37° C., pH 7.4, under 1 g resting tension. The segments were exposed to 50 mM KCl to evoke contraction. After thorough washing, cumulative concentration-effect curves to angiotensin II were constructed. Then, test compounds were preincubated with the tissue and a second concentration-effect curve to angiotensin II was constructed. A dextral shift in the concentration-effect curve to angiotensin II, greater than that seen in appropriate time controls, was taken as antagonistic activity of the test compound.

The compounds of the present invention were active as antagonists of angiotensin II-mediated contraction in this assay.

(b) Isolated segments of guinea pig ileum were set up in Krebs' physiological salt solution at 37° C., pH 7.4, under 1 g resting tension. Cumulative concentration-effect curves to angiotensin II were constructed using 0.5 log unit increases in concentration. Then, test compounds were pre-incubated with the tissue and a second concentration-effect curve to angiotensin II was constructed. A dextral shift in the concentration-effect curve to angiotensin II, greater than that seen in appropriate time controls, was taken as antagonistic activity of the test compound.

The compounds of the present invention were active as antagonists of angiotensin II-mediated contraction in this assay.

EXAMPLE 19

Determination of Antihypertensive Activity (a) Male normotensive rats were subjected to complete left renal artery ligation. Four to 8 days post ligation, systemic blood pressure and heart rate were recorded via the left femoral artery from conscious rats housed in Bollman restraint cages. Test and control compounds were administered via the femoral vein. The rats were divided into test and control groups.

For intravenous administration, the test group received the test compound (in a vehicle of Tween ®80 [polyoxyethylene sorbitan monooleate] and normal saline) in a dose of 10 or 30 mg/kg, whereas the control group received the appropriate volume of vehicle. Blood pressure and heart rate were monitored for 4 hours, at which time captopril (3 mg/kg, iv) was administered to both groups as a positive control, and blood pressure and heart rate were recorded for a further 30 minutes.

For oral administration, the test group received a dose of 10 or 30 mg of the test compound, whereas the control group received the appropriate volume of vehicle. Blood pressure and heart rate were monitored for 4 hours, at which time captopril (3 mg/kg, iv) was administered to both groups as a positive control and the same parameters were recorded for a further 30 minutes.

The compounds of Formula (I), (II) and (III) significantly lowered mean blood pressure when given by both the intravenous and oral routes.

(b) Normotensive rats were set-up for recording systemic blood pressure and heart rate as described for renal hypertensive rats in (a) above. angiotensin II (0.1 μg/kg, iv) was administered intravenously to both control and test groups at 15 and 30 minutes prior to administration of vehicle or test compound, which was administered by bolus injection or infusion. Angiotensin II (0.1 μg/kg, iv) was then injected every 30 minutes for 4 hours. A final dose of angiotensin II (1.0 μg/kg, iv) was given at the end of the experiment.

The compounds of the present invention inhibited significantly the pressor response to angiotensin II without causing sustained hypotension, demonstrating that the compounds possess angiotensin II blocking properties in vivo and that their hypotensive action is selective to angiotensin II-dependent hypotension. (The systemic blood pressure of normotensive rats is not angiotensin II-dependent.)

EXAMPLE 20

Cognitive Enhancement Assay

The following describes a model to determine the cognitive enhancing effects of compounds of Formulae (I), (II) and (III).

Sprague Dawley rats (240–260 g) were kept in the laboratory the night prior to testing, and remained there throughout the experiment. The Morris Water Maze consists of a circular pool made from black perspex (122 cm diameter, 46 cm in height, with a 15 cm rim), filled with opaque water to a height of 35 cm. A hidden platform consisting of black plexiglass was placed 1–2 cm below the surface of the water. The pool was divided into four quadrants, arbitrarily corresponding to north, south, east and west. The platform was located in the south quadrant, about 24 cm from the side. Objects of high contrast were placed about the room to serve as spatial cues. A TV camera tracked the swim path of the rats, and the data thus obtained was examined to determine the time in seconds the rats took to find the platform (escape latency). Test trials were initiated by placing a rat into one of the four quadrants, facing the wall. Testing consisted of a block of six trials (starting first in the north quadrant, then east, south, west, north, and finally east) on each of two consecutive days. During each trial the rat was allowed 90 seconds to find the platform. When the rat successfully found the platform, it was given 30 seconds to "study" the spatial cues. When the rat failed to find the platform within 90 seconds, it was given a score of 90 seconds, and placed on the platform for 30 seconds.

The following groups of 8 rats each were used: 1) vehicle-treated controls; 2) atropine treated-controls; 3) atropine plus test drug. Thus the studies were designed to determine whether the test drug could alleviate the cognitive deficit induced by atropine (30 mg/kg, ip). Statistical tests were applied to test for heterogeneity of the learning curves, and separation of the learning curves.

The compounds of the present invention were active as cognitive enhancing agents in this assay.

While the present invention has been described with respect to specific embodiments thereof, it will be understood by those skilled in the art that various changes may be made and equivalents may be substituted without departing from the true spirit and scope of the invention. All such modifications are intended to be within the scope of the claims appended hereto.

What is claimed is:

1. A compound represented by the Formula (I):

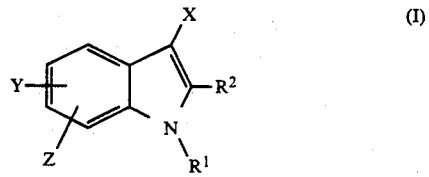

$R^1$ is lower alkyl;
$R^2$ is 2''-(1H-tetrazol-5-yl)biphenyl-4'-ylmethyl;
X is hydrogen, lower alkyl, halogen, —C(O)CF$_3$, —CO$_2$R$^4$, or —C(O)NR$^5$R$^6$;
Y is hydrogen, lower alkyl, lower alkoxy, hydroxy, halogen, or —CO$_2$R$^4$;
Z is hydrogen, lower alkyl, lower alkoxy, or halogen; wherein
$R^4$ is hydrogen or lower alkyl;
$R^5$ is hydrogen or lower alkyl;
$R^4$ is hydrogen or lower alkyl; or
$R^5$ and $R^6$ taken together with the nitrogen to which they attached represent a heterocycle;
or a pharmaceutically acceptable salt thereof.

2. The compound (I) of claim 1 wherein Z is hydrogen, or a pharmaceutically acceptable salt thereof.

3. The compound of claim 2 wherein Y is hydrogen or lower alkoxy, or a pharmaceutically acceptable salt thereof.

4. The compound of claim 3 wherein X is —CO$_2$R$^4$, or a pharmaceutically acceptable salt thereof.

5. The compound of claim 4 wherein $R^1$ is n-butyl, $R^4$ is hydrogen, and Y is hydrogen, namely 1-(n-butyl)-2-[2''-(1H-tetrazol-5-yl)biphenyl-4'-ylmethyl]indole-3-carboxylic acid, or a pharmaceutically acceptable salt thereof.

6. The compound of claim 4 wherein $R^1$ is n-butyl, $R^4$ is hydrogen, and Y is 5-methoxy, namely 1-(n-butyl)-5-methoxy-2-[2''-(1H-tetrazol-5-yl)biphenyl-4'-ylmethyl]indole-3-carboxylic acid, or a pharmaceutically acceptable salt thereof.

7. A pharmaceutical composition comprising a therapeutically effective amount of a compound of claim 1, or a pharmaceutically acceptable salt thereof, in admixture with one or more pharmaceutically acceptable non-toxic carriers.

8. A method for treating a mammal having a disease state that is alleviable by treatment with an angiotensin II antagonist, which comprises administering to a mammal in need thereof a therapeutically effective amount of a compound of claim 1, or a pharmaceutically acceptable salt thereof.

9. The method of claim 8, wherein the disease state is hypertension or congestive heart failure.

10. The method of claim 8, wherein the disease state is chronic renal failure or a disorder of the alimentary tract.

11. The method of claim 8, wherein the disease state is a cognitive or an affective disorder.

* * * * *

UNITED STATES PATENT AND TRADEMARK OFFICE
CERTIFICATE OF CORRECTION

PATENT NO. : 5,212,195
DATED : May 18, 1993
INVENTOR(S) : Clark, et al.

It is certified that error appears in the above-identified patent and that said Letters Patent is hereby corrected as shown below:

Title page, item [54] and col. 1, lines 1-3,

The Title: "SUBSTITUTED INDOLE ANTAGONISTS DERIVATIVES WHICH ARE ANGIOTENSIN II" should read --SUBSTITUTED INDOLE DERIVATIVES WHICH ARE ANGIOTENSIN II ANTAGONISTS--

Claim 1, at column 65, lines 34-35: "$R^1$ is lower alkyl;" should read --wherein:
  $R^1$ is lower alkyl;--

Claim 1, at column 66, line 3 "$R^4$ is hydrogen or lower alkyl; or" should read --$R^6$ is hydrogen or lower alkyl; or--

Signed and Sealed this

First Day of November, 1994

*Attest:*

*Attesting Officer*

BRUCE LEHMAN
*Commissioner of Patents and Trademarks*